(12) United States Patent
Dong et al.

(10) Patent No.: US 8,236,759 B2
(45) Date of Patent: Aug. 7, 2012

(54) GLP-1 PHARMACEUTICAL COMPOSITIONS

(75) Inventors: Zheng Xin Dong, Holliston, MA (US); Roland Cherif-Cheikh, Barcelona (ES); Resurreccion Alloza Miravete, Amer (ES); Jose-Antonio Cordero Rigol, Rubi (ES); Frederic Lacombe, Sant Cugat del Valles (ES); Maria Dolores Tobalina Maestre, Barcelona (ES)

(73) Assignee: Ipsen Pharma SAS, Paris (FR)

( * ) Notice: Subject to any disclaimer, the term of this patent is extended or adjusted under 35 U.S.C. 154(b) by 969 days.

(21) Appl. No.: 11/479,074

(22) Filed: Jun. 30, 2006

(65) Prior Publication Data

US 2007/0021339 A1 Jan. 25, 2007

Related U.S. Application Data

(60) Provisional application No. 60/696,142, filed on Jun. 30, 2005.

(51) Int. Cl.
  *A61K 38/26* (2006.01)
(52) U.S. Cl. .................. 514/7.2; 514/21.3; 530/324
(58) Field of Classification Search .............. 530/308, 530/324; 514/2, 7.2, 21.3
See application file for complete search history.

(56) References Cited

U.S. PATENT DOCUMENTS

| | | | |
|---|---|---|---|
| 4,591,496 A * | 5/1986 | Cohen et al. ................ 424/467 |
| 4,810,501 A * | 3/1989 | Ghebre-Sellassie et al. . 424/469 |
| 5,271,945 A * | 12/1993 | Yoshioka et al. ............ 424/489 |
| 5,480,868 A * | 1/1996 | Kamei et al. ................ 514/10.3 |
| 5,575,987 A * | 11/1996 | Kamei et al. ................ 424/451 |
| 5,614,487 A * | 3/1997 | Battersby et al. ............ 514/8.5 |
| 5,665,394 A * | 9/1997 | Igari et al. ................... 424/501 |
| 5,705,483 A | 1/1998 | Galloway et al. |
| 5,776,885 A * | 7/1998 | Orsolini et al. .............. 424/491 |
| 6,258,382 B1 * | 7/2001 | Takaoka et al. .............. 424/486 |
| 6,380,357 B2 | 4/2002 | Hermeling et al. |
| 6,458,387 B1 * | 10/2002 | Scott et al. ................... 424/489 |
| 6,482,864 B1 | 11/2002 | Yamagata et al. |
| 6,555,521 B2 | 4/2003 | Hermeling et al. |
| 6,566,490 B1 | 5/2003 | Manique et al. |
| 6,903,186 B1 | 6/2005 | Dong |
| 7,323,169 B2 * | 1/2008 | Goldenberg et al. ...... 424/130.1 |
| 7,521,527 B2 | 4/2009 | Dong et al. |
| 7,563,871 B2 * | 7/2009 | Wright et al. ................. 530/350 |
| 7,612,176 B2 * | 11/2009 | Wright et al. ................. 530/350 |
| 2001/0006943 A1 | 7/2001 | Jensen et al. |
| 2002/0165342 A1 | 11/2002 | Galloway et al. |
| 2003/0045464 A1 | 3/2003 | Hermeling et al. |
| 2003/0050237 A1 | 3/2003 | Kim et al. |
| 2003/0186858 A1 | 10/2003 | Arentsen |

FOREIGN PATENT DOCUMENTS

| | | |
|---|---|---|
| EP | 0 619 322 | 10/1994 |
| EP | 0 658 568 | 6/1995 |
| EP | 0 733 644 | 9/1996 |
| WO | 99/43705 | 9/1999 |
| WO | 00/34331 | 6/2000 |
| WO | 01/00223 | 1/2001 |
| WO | 01/57084 | 8/2001 |
| WO | WO 01/98331 | 12/2001 |
| WO | WO 02/47715 | 6/2002 |
| WO | 03/035099 | 5/2003 |
| WO | 2005/058252 | 6/2005 |
| WO | WO 2005/112949 | 12/2005 |

OTHER PUBLICATIONS

Choi et al., "Control of blood glucose by novel GLP-1 delivery using biodegradable triblock copolymer of PLGA-PEG-PLGA in type 2 diabetic rats," Pharm. Res., 2004, 21:827-831.
Deacon, C. et al., "Dipeptidyl peptidase IV resistant analogues of glucagons-like peptide-1 which have extended metabolic stability and improved biological activity," Diabetologia, 1998, 41:271-278.
Kim et al., "The application of crystal soaking technique to study the effect of zinc and cresol on insulinotropin crystals grown from a saline solution," Pharma. Res., 1995, 12(11):1664-1670.
Parker, J. et al., "Structure-function analysis of a series of glucagons-like peptide-1 analogs," J. Peptide Res., 1998, 52:398-409.
Pridal et al., "Absorption of glucagons-like peptide-1 can be protracted by zinc or protamine," Int. J. Pharmaceutics, 1996, 136:53-59.

* cited by examiner

*Primary Examiner* — David Lukton
(74) *Attorney, Agent, or Firm* — Hunton & Williams LLP (57) ABSTRACT

The present invention is directed to peptide analogues of glucagon-like peptide-1, the pharmaceutically-acceptable salts thereof, to methods of using such analogues to treat mammals and to pharmaceutical compositions useful therefore comprising said analogues.

45 Claims, 7 Drawing Sheets

GLP-1 PHARMACEUTICAL COMPOSITIONS

RELATED APPLICATION

This application claims priority to U.S. Provisional application No. 60/696,142 filed Jun. 30, 2006.

BACKGROUND OF THE INVENTION

The present invention is directed to peptide analogues of glucagon-like peptide-1, the pharmaceutically-acceptable salts thereof, to methods of using such analogues to treat mammals and to pharmaceutical compositions useful therefore comprising said analogues.

Glucagon-like peptide-1(7-36) amide (GLP-1) is synthesized in the intestinal L-cells by tissue-specific post-translational processing of the glucagon precursor preproglucagon (Varndell, J. M., et al., J. Histochem Cytochem, 1985:33: 1080-6) and is released into the circulation in response to a meal. The plasma concentration of GLP-1 rises from a fasting level of approximately 15 pmol/L to a peak postprandial level of 40 pmol/L. It has been demonstrated that, for a given rise in plasma glucose concentration, the increase in plasma insulin is approximately threefold greater when glucose is administered orally compared with intravenously (Kreymann, B., et al., Lancet 1987:2, 1300-4). This alimentary enhancement of insulin release, known as the incretin effect, is primarily humoral and GLP-1 is thought to be the most potent physiological incretin in humans. In addition to the insulinotropic effect, GLP-1 suppresses glucagon secretion, delays gastric emptying (Wettergren A., et al., Dig Dis Sci 1993:38:665-73) and may enhance peripheral glucose disposal (D'Alessio, D. A. et al., J. Clin Invest 1994:93:2293-6).

In 1994, the therapeutic potential of GLP-1 was suggested following the observation that a single subcutaneous (s/c) dose of GLP-1 could completely normalize postprandial glucose levels in patients with non-insulin-dependent diabetes mellitus (NIDDM) (Gutniak, M. K., et al., Diabetes Care 1994:17:1039-44). This effect was thought to be mediated both by increased insulin release and by a reduction in glucagon secretion. Furthermore, an intravenous infusion of GLP-1 has been shown to delay postprandial gastric emptying in patients with NIDDM (Williams, B., et al., J. Clin Endo Metab 1996:81:327-32). Unlike sulphonylureas, the insulinotropic action of GLP-1 is dependent on plasma glucose concentration (Holz, G. G. $4^{th}$, et al., Nature 1993:361:362-5). Thus, the loss of GLP-1-mediated insulin release at low plasma glucose concentration protects against severe hypoglycemia. This combination of actions gives GLP-1 unique potential therapeutic advantages over other agents currently used to treat NIDDM.

Numerous studies have shown that when given to healthy subjects, GLP-1 potently influences glycemic levels as well as insulin and glucagon concentrations (Orskov, C, Diabetologia 35:701-711, 1992; Hoist, J. J., et al., *Potential of GLP-1 in diabetes management* in Glucagon III, Handbook of Experimental Pharmacology, Lefevbre P J, Ed. Berlin, Springer Verlag, 1996, p. 311-326), effects which are glucose dependent (Kreymann, B., et al., Lancet ii: 1300-1304, 1987; Weir, G. C., et al., Diabetes 38:338-342, 1989). Moreover, it is also effective in patients with diabetes (Gutniak, M., N. Engl J Med 226:1316-1322, 1992; Nathan, D. M., et al., Diabetes Care 15:270-276, 1992), normalizing blood glucose levels in type 2 diabetic subjects (Nauck, M. A., et al., Diabetologia 36:741-744, 1993), and improving glycemic control in type 1 patients (Creutzfeldt, W. O., et al., Diabetes Care 19:580-586, 1996), demonstrating its ability to, inter alia, increase insulin sensitivity/reduce insulin resistance. GLP-1 and agonists thereof have been proposed for use in subjects at risk for developing non-insulin dependent diabetes (see WO 00/07617) as well as for the treatment of gestational diabetes mellitus (U.S. Patent Pub. No. 20040266670).

In addition to the foregoing, there are a number of therapeutic uses in mammals, e.g., humans, for which GLP-1 and agonists thereof have been suggested, including, without limitation: improving learning, enhancing neuro-protection, and/or alleviating a symptom of a disease or disorder of the central nervous system, e.g., through modulation of neurogenesis, and e.g., Parkinson's Disease, Alzheimer's Disease, Huntington's Disease, ALS, stroke, ADD, and neuropsychiatric syndromes (U.S. Patent Pub. No.'s 20050009742 and 20020115605); converting liver stem/progenitor cells into functional cells pancreatic (WO03/033697); preventing beta-cell deterioration (U.S. Patent Pub. No.'s 20040053819 and 20030220251) and stimulation of beta-cell proliferation (U.S. Patent Pub. No. 20030224983); treating obesity (U.S. Patent Pub. No. 20040018975; WO98/19698); suppressing appetite and inducing satiety (U.S. Patent Pub. No. 20030232754); treating irritable bowel syndrome (WO 99/64060); reducing the morbidity and/or mortality associated with myocardial infarction (US Patent Pub No. 20040162241, WO98/08531) and stroke (see WO 00/16797); treating acute coronary syndrome characterized by an absence of Q-wave myocardial infarction (U.S. Patent Pub. No. 20040002454); attenuating post-surgical catabolic changes (U.S. Pat. No. 6,006,753); treating hibernating myocardium or diabetic cardiomyopathy (U.S. Patent Pub. No. 20050096276); suppressing plasma blood levels of norepinepherine (U.S. Patent Pub. No. 20050096276); increasing urinary sodium excretion, decreasing urinary potassium concentration (U.S. Patent Pub. No. 20050037958); treating conditions or disorders associated with toxic hypervolemia, e.g., renal failure, congestive heart failure, nephrotic syndrome, cirrhosis, pulmonary edema, and hypertension (U.S. Patent Pub. No. 20050037958); inducing an inotropic response and increasing cardiac contractility (U.S. Patent Pub. No. 20050037958); treating polycystic ovary syndrome (U.S. Patent Pub. No.'s 20040266678 & 20040029784); treating respiratory distress (U.S. Patent Pub. No. 20040235726); improving nutrition via a non-alimentary route, i.e., via intravenous, subcutaneous, intramuscular, peritoneal, or other injection or infusion (U.S. Patent Pub. No. 20040209814); treating nephropathy (U.S. Patent Pub. No. 20040209803); treating left ventricular systolic dysfunction, e.g., with abnormal left ventricular ejection fraction. (U.S. Patent Pub. No. 20040097411); inhibiting antro-duodenal motility, e.g., for the treatment or prevention of gastrointestinal disorders such as diarrhea, postoperative dumping syndrome and irritable bowel syndrome, and as premedication in endoscopic procedures (U.S. Patent Pub. No. 20030216292); treating critical illness polyneuropathy (CIPN) and systemic inflammatory response syndrome (SIRS) (U.S. Patent Pub. No. 20030199445); modulating triglyceride levels and treating dyslipidemia (U.S. Patent Pub. No.'s 20030036504 and 20030143183); treating organ tissue injury caused by reperfusion of blood flow following ischemia (U.S. Patent Pub. No. 20020147131); treating coronary heart disease risk factor (CHDRF) syndrome (U.S. Patent Pub. No. 20020045636); and others.

GLP-1 is, however, metabolically unstable, having a plasma half-life ($t_{1/2}$) of only 1-2 min in vivo. Exogenously administered GLP-1 is also rapidly degraded (Deacon, C. F., et al., Diabetes 44:1126-1131, 1995). This metabolic instability limits the therapeutic potential of native GLP-1. A number of attempts have been taken to improve the therapeutic potential of GLP-1 and its analogs through improvements in formulation. For example, International patent publication no. WO 01/57084 describes a process for producing crystals of GLP-1 analogues which are said to be useful in the preparation of pharmaceutical compositions, such as injectable drugs, comprising the crystals and a pharmaceutical acceptable carrier. Heterogeneous micro crystalline clusters of GLP-1(7-37)OH have been grown from saline solutions and examined after crystal soaking treatment with zinc and/or m-cresol (Kim and Haren, Pharma. Res. Vol. 12 No. 11 (1995)). Crude crystalline suspensions of GLP(7-36)NH$_2$ containing needle-like crystals and amorphous precipitation have been prepared from phosphate solutions containing zinc or protamine (Pridal, et. al., International Journal of Pharmaceutics Vol. 136, pp. 53-59 (1996)). European patent publication no. EP 0619322A2 describes the preparation of microcrystalline forms of GLP-1(7-37)OH by mixing solutions of the protein in pH 7-8.5 buffer with certain combinations of salts and low molecular weight polyethylene glycols (PEG). U.S. Pat. No. 6,566,490 describes seeding microcrystals of, inter alia, GLP-1 which are said to aid in the production of purified peptide products. U.S. Pat. No. 6,555,521 (U.S. '521) discloses GLP-1 crystals having a tetragonal flat rod or a plate-like shape which are said to have improved purity and to exhibit extended in vivo activity. U.S. '521 teaches that such crystals are relatively uniform and remain in suspension for a longer period of time than prior crystalline clusters and amorphous crystalline suspensions which were said to settle rapidly, aggregate or clump together, clog syringe needles and generally exacerbate unpredictable dosing.

A biodegradable triblock copolymer of poly[(dl-lactide-co-glycolide)-β-ethylene glycol-β-(-lactide-co-glycolide)] has been suggested for use in a controlled release formulation of GLP-1. However like other polymeric systems, the manufacture of triblock copolymer involves complex protocols and inconsistent particulate formation.

Similarly, biodegradable polymers, e.g., poly(lactic-co-glycolic acid) (PLGA), have also been suggested for use in sustained delivery formulations of peptides. However the use of such biodegradable polymers has been disfavored in the art since these polymers generally have poor solubility in water and require water-immiscible organic solvents, e.g., methylene chloride, and/or harsh preparation conditions during manufacture. Such organic solvents and/or harsh preparation conditions are considered to increase the risk of inducing conformational change of the peptide or protein of interest, resulting in decreased structural integrity and compromised biological activity (Choi et al., Pharm. Research, Vol. 21, No. 5, (2004).) Poloxamers have been likewise faulted. (Id.)

The GLP-1 compositions described in the foregoing references are less than ideal for preparing pharmaceutical formulations of GLP's since they tend to trap impurities and/or are otherwise difficult to reproducibly manufacture and administer. Also, GLP analogs are known to induce nausea at elevated concentrations, thus there is a need to provide a sustained drug effect with reduced initial plasma concentrations. Hence, there is a need for GLP-1 formulations which are more easily and reliably manufactured, that are more easily and reproducibly administered to a patient, and that provide for reduced initial plasma concentrations in order to reduce or eliminate unwanted side-effects.

SUMMARY OF THE INVENTION

The invention may be summarized in the following paragraphs as well as the claims. Accordingly, it is a first object of the invention to provide a pharmaceutical composition comprising a GLP-1 analog according to formula (I):

$$(Aib^{8,35})hGLP-1(7-36)NH_2 \qquad (I)$$

or a pharmaceutically acceptable salt thereof, wherein the formulation of said composition provides for superior manufacturing, administration, pharmacokinetic and pharmacodynamic properties, as well as attenuated negative side-effects. Preferably the pharmaceutical composition of the invention does not consist of a clear aqueous ZnCl$_2$ solution having pH 4 in which said [Aib$^{8,35}$]hGLP-1(7-36)NH$_2$ is present at a concentration of 4 mg/ml and said ZnCl$_2$ is present at a concentration of 0.5 mg/ml.

In a first aspect of said first object the invention provides for a pharmaceutical composition having an improved drug release profile, preferably with a reduced initial burst.

In a second aspect of said first object the invention provides for pharmaceutical composition comprising a compound of formula (I) having an extended duration of action.

In a third aspect of said first object the invention provides for a pharmaceutical composition comprising a compound of formula (I) or a pharmaceutically acceptable salt thereof and a pharmaceutically acceptable carrier or diluent. Preferably said carrier or diluent comprises water.

In a first preferred embodiment of said third aspect of said first object said pharmaceutical composition further comprises zinc. More preferably, the zinc in said pharmaceutical composition is present in a concentration from about 0.0005 mg/mL to about 50 mg/m. Even more preferably, the zinc in said pharmaceutical composition is present in a concentration from about 0.01 mg/ml to about 0.50 mg/ml. More preferably, said pharmaceutical composition comprises a diluent, wherein said diluent comprises a pharmaceutically acceptable aqueous solution. The diluent may comprise sterile water.

More preferably, said pharmaceutical composition comprises an aqueous mixture, suspension or solution, wherein said compound of formula (I) is present at a concentration of approximately 0.5%-30% (w/w). More preferably the concentration of said compound of formula (I) in said aqueous mixture, suspension or solution is approximately 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% (w/w). More preferably, the concentration of said compound of formula (I) in said aqueous solution is approximately 1%, 2%, 3%, 4%, 5%, 6%, 7%, 8%, 9%, 10%, 11%, 14%, 15%, 16%, 19%, 20%, 21%, 22%, 23%, 24%, 25%, 26%, 29%, or 30% (w/w). More preferably still, the concentration of said compound of formula (I) in said aqueous solution is approximately 1%, 2%, 3%, 4%, 5%, 6%, 9%, 10%, 11%, 22%, 23%, 24%, 25%, or 26% (w/w). Even more preferably still, the concentration of said compound of formula (I) in said aqueous solution is approximately 1%, 2%, 3%, 4%, 5%, 6%, 10%, 22%, 23%, 24%, 25%, or 26% (w/w). Still more preferably, the concentration of said compound of formula (I) in said aqueous solution is approximately 1%, 2%, 5%, 10%, 23% or 25% (w/w). By "approximately" is meant the following: for concentrations of about 0.5% to about 4%, ±0.5% of the target value is the desired range (for example, 0.5% to 1.5% is approximately 1%); for target concentrations of about 5% and higher, 20% of the target value is the desired range (for example, 8% to 12% is approximately 10%).

In a second preferred embodiment of said third aspect of said first object, said pharmaceutical composition further comprises zinc, wherein the molar ratio of said compound of formula (I) to zinc in said pharmaceutical composition ranges from approximately 6:1 to approximately 1:1. More preferably, said ratio ranges from approximately 5.5:1 to approximately 1:1. More preferably still, said ratio ranges from approximately 5.4:1 to approximately 1.5:1. Even more preferably still, said ratio is approximately 5.4:1, 4.0:1, or 1.5:1. Most preferably, said ratio is approximately 1.5:1. What is meant by approximately in this aspect of the invention is a ratio of 1.5:1±10% each target value, thus expected ratios include ratios encompassing, e.g., 1.35-1.65:0.85-1.15.

Preferably, in said second preferred embodiment of said third aspect of said first object of the invention, the concentration of [Aib$^{8,35}$]hGLP-1(7-36)NH$_2$ in said pharmaceutical composition is about 1% (weight/volume) and the molar ratio of [Aib$^{8,35}$]hGLP-1(7-36)NH$_2$ to zinc is about 1.5:1. Also preferably, in said second preferred embodiment of said third aspect of said first object of the invention, the concentration of [Aib$^{8,35}$]hGLP-1(7-36)NH$_2$ in said pharmaceutical composition is about 2% (weight/volume) and the molar ratio of [Aib$^{8,35}$]hGLP-1(7-36)NH$_2$ to zinc is about 1.5:1. Further preferably, in said second preferred embodiment of said third aspect of said first object of the invention, the concentration of [Aib$^{8,35}$]hGLP-1(7-36)NH$_2$ in said pharmaceutical composition is about 10% (weight/volume) and the molar ratio of [Aib$^{8,35}$]hGLP-1(7-36)NH$_2$ to zinc is about 1.5:1. Still further preferably, in said second preferred embodiment of said third aspect of said first object of the invention, the concentration of [Aib$^{8,35}$]hGLP-1(7-36)NH$_2$ in said pharmaceutical composition is about 23% or about 25% (weight/volume). and the molar ratio of [Aib$^{8,35}$]hGLP-1(7-36)NH$_2$ to zinc is about 1.5:1.

Preferably, in said second preferred embodiment of said third aspect of said first object of the invention, the concentration of [Aib$^{8,35}$]hGLP-1(7-36)NH$_2$ in said pharmaceutical composition is about 5% (weight/volume) and said ratio is approximately 5.4:1. Also preferably in said second preferred embodiment of said third aspect of said first object of the invention, the concentration of [Aib$^{8,35}$]hGLP-1(7-36)NH$_2$ in said composition is about 5% (weight/volume) and said ratio is approximately 4.0:1. Also preferably in said second preferred embodiment of said third aspect of said first object of the invention, the concentration of [Aib$^{8,35}$]hGLP-1(7-36)NH$_2$ in said composition is about 10% (weight/volume) and said ratio is approximately 5.4:1. Still further preferably, in said second preferred embodiment of said third aspect of said first object of the invention, the concentration of [Aib$^{8,35}$]hGLP-1(7-36)NH$_2$ in said composition is about 10% (weight/volume) and said ratio is approximately 4.0:1.

Preferably, in said second preferred embodiment of said third aspect of said first object, said zinc is provided as zinc chloride or zinc acetate. More preferably, said zinc acetate is provided as ZnAc$_2$.2H$_2$O.

Preferably, in both of said first and second preferred embodiments of said third aspect of said first object, the pH of said pharmaceutical composition is adjusted upward using a base. More preferably, said pH adjustment is made using NaOH. More preferably still, the pH of said pharmaceutical composition is adjusted with NaOH such that, when diluted to approximately ½ initial concentration using 0.9% NaCl, a pH value of approximately 5.0-5.5 is obtained using direct potentiometric determination.

As will be appreciated by one of skill in the art of pharmaceutical formulations, the pH of a composition of the invention may be adjusted even more broadly than outlined above using appropriate pharmaceutically acceptable acids and bases. Such further adjustment of pH of the final composition allows for modulating parameters such as, e.g., peptide concentration, zinc concentration, and in vivo release profile.

In a first preferred embodiment of said second aspect of said first object, the invention features a pharmaceutical composition according to said third aspect, including, independently for each occurrence, each of said preferred embodiments of said third aspect, wherein the composition is formulated such that the compound according to formula (I) is released within a subject in need thereof, e.g., a mammal, preferably a human, for an extended period of time. Preferably said release of said compound extends for at least one hour, more preferably at least 4, 6, 12, or 24 hours. More preferably still, said composition is formulated such that the compound according to formula (I) is released within a subject for at least 36, 48, 60, 72, 84, or 96 hours. More preferably still, said composition is formulated such that the compound according to formula (I) is released within a subject for at least approximately 5, 6, 7, 8, 9, 10, 11, 12, 13, or 14 days. More preferably still, said composition is formulated such that the compound according to formula (I) is released within a subject for at least approximately 2, 3 or 4 weeks. Even more preferably, said composition is formulated such that the compound according to formula (I) is released within a subject for at least approximately 1, 1.5, 2, or 3 months, or longer.

It is a second object of the present invention to provide for a method of eliciting a GLP-1 agonist effect, said method comprising contacting a receptor of the GLP-1(7-36)NH$_2$ ligand with the compound according to formula (I), said compound according to formula (I) being provided to said receptor, directly or indirectly, via a composition according to said third aspect, including, independently for each occurrence, each of said preferred embodiments of said third aspect.

In a first preferred embodiment of said second object of the invention, said receptor of the GLP-1(7-36)NH$_2$ ligand is present in an animal subject, preferably a primate, more preferably a human being. Thus, in this embodiment the present invention provides a method of eliciting an agonist effect from a GLP-1 receptor in a subject in need thereof which comprises administering to said subject a composition of the instant invention, wherein said composition comprises an effective amount of a compound of formula (I) or a pharmaceutically acceptable salt thereof.

In a more preferred embodiment of said second object of the invention, said subject is a human afflicted with, or at risk of developing, a disease or condition selected from the group consisting of Type I diabetes, Type II diabetes, gestational diabetes, obesity, excessive appetite, insufficient satiety, and metabolic disorder. Preferably said disease is Type I diabetes or Type II diabetes.

In another more preferred embodiment of said second object of the invention, said subject is a human afflicted with, or at risk of developing, a disease selected from the group consisting of Type I diabetes, Type II diabetes, obesity, glucagonomas, secretory disorders of the airway, arthritis, osteoporosis, central nervous system disease, restenosis, neurodegenerative disease, renal failure, congestive heart failure, nephrotic syndrome, cirrhosis, pulmonary edema, hypertension, and disorders wherein the reduction of food intake is desired, a disease or disorder of the central nervous system, (e.g., through modulation of neurogenesis, and e.g., Parkinson's Disease, Alzheimer's Disease, Huntington's Disease, ALS, stroke, ADD, and neuropsychiatric syndromes), irritable bowel syndrome, myocardial infarction (e.g., reducing the morbidity and/or mortality associated therewith), stroke, acute coronary syndrome (e.g., characterized by an absence of Q-wave) myocardial infarction, post-surgical catabolic changes, hibernating myocardium or diabetic cardiomyopathy, insufficient urinary sodium excretion, excessive urinary potassium concentration, conditions or disorders associated with toxic hypervolemia, (e.g., renal failure, congestive heart failure, nephrotic syndrome, cirrhosis, pulmonary edema, and hypertension), polycystic ovary syndrome, respiratory distress, nephropathy, left ventricular systolic dysfunction, (e.g., with abnormal left ventricular ejection fraction), gastrointestinal disorders such as diarrhea, postoperative dumping syndrome and irritable bowel syndrome, (i.e., via inhibition of antro-duodenal motility), critical illness polyneuropathy (CIPN), systemic inflammatory response syndrome (SIRS), dyslipidemia, organ tissue injury caused by reperfusion of blood flow following ischemia, and coronary heart disease risk factor (CHDRF) syndrome.

In another aspect of said second object, the invention features a method of converting liver stem/progenitor cells into functional pancreatic cells, of preventing beta-cell deterioration and of stimulating beta-cell proliferation, of suppressing plasma blood levels of norepinepherine, of inducing an inotropic response and of increasing cardiac contractility, of improving nutrition via a non-alimentary route, (e.g., via intravenous, subcutaneous, intramuscular, peritoneal, or other injection or infusion rout), of pre-treating a subject to undergo an endoscopic procedures, and of modulating triglyceride levels, in a subject in need thereof, said method comprising administering to said subject a formulation of the present invention comprising an effective amount of a compound of formula (I) or a pharmaceutically acceptable salt thereof. Preferably said subject is a mammalian animal, more preferably a primate, more preferably still a human being.

DETAILED DESCRIPTION

A peptide of this invention is denoted herein by the following format, e.g., (Aib$^{8,35}$)hGLP-1(7-36)NH$_2$, with the substituted amino acids from the natural sequence placed between the first set of parentheses (e.g., Aib$^{8,35}$ denotes that Aib is substituted for Ala$^8$ and Gly$^{35}$ in hGLP-1). Aib is the abbreviation for α-aminoisobutyric acid. The abbreviation GLP-1 means glucagon-like peptide-1; hGLP-1 means human glucagon-like peptide-1. The numbers between the second set of parentheses refer to the number of amino acids present in the peptide (e.g., hGLP-1(7-36) refers to amino acids 7 through 36 of the peptide sequence for human GLP-1). The sequence for hGLP-1(7-37) is listed in Mojsov, S., Int. J. Peptide Protein Res., 40, 1992, pp. 333-342. The designation "NH$_2$" in hGLP-1(7-36)NH$_2$ indicates that the C-terminus of the peptide is amidated. hGLP-1(7-36) means that the C-terminus is the free acid. In hGLP-1(7-38), residues in positions 37 and 38 are Gly and Arg, respectively, unless otherwise indicated.

The peptides used in this invention advantageously may be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids). A typical method of making a salt of a peptide of the present invention is well known in the art and can be accomplished by standard methods of salt exchange. Accordingly, the TFA salt of a peptide of the present invention (the TFA salt results from the purification of the peptide by using preparative HPLC, eluting with TFA containing buffer solutions) can be converted into another salt, such as an acetate salt by dissolving the peptide in a small amount of 0.25 N acetic acid aqueous solution. The resulting solution is applied to a semi-prep HPLC column (Zorbax, 300 SB, C-8). The column is eluted with (1) 0.1N ammonium acetate aqueous solution for 0.5 hrs., (2) 0.25N acetic acid aqueous solution for 0.5 hrs. and (3) a linear gradient (20% to 100% of solution B over 30 min.) at a flow rate of 4 ml/min (solution A is 0.25N acetic acid aqueous solution; solution B is 0.25N acetic acid in acetonitrile/water, 80:20). The fractions containing the peptide are collected and lyophilized to dryness.

As is well known to those skilled in the art, the known and potential uses of GLP-1 are varied and multitudinous (See, Todd, J. F., et al., Clinical Science, 1998, 95, pp. 325-329; and Todd, J. F. et al., European Journal of Clinical Investigation, 1997, 27, pp. 533-536). Thus, the administration of the compounds of this invention for purposes of eliciting an agonist effect can have the same effects and uses as GLP-1 itself. These varied uses of GLP-1 may be summarized as follows, treatment of: Type I diabetes, Type II diabetes, obesity, glucagonomas, secretory disorders of the airway, metabolic disorder, arthritis, osteoporosis, central nervous system diseases, restenosis, neurodegenerative diseases, renal failure, congestive heart failure, nephrotic syndrome, cirrhosis, pulmonary edema, hypertension, disorders wherein the reduction of food intake is desired, as well as the various other conditions and disorders discussed herein. Accordingly, the present invention includes within its scope pharmaceutical compositions as defined herein comprising, as an active ingredient, a compound of formula (I).

The dosage of active ingredient in the formulations of this invention may be varied; however, it is necessary that the amount of the active ingredient be such that a suitable dosage is obtained. The selected dosage depends upon the desired therapeutic effect, on the route of administration, and on the duration of the treatment, and normally will be determined by the attending physician. In general, an effective dosage for the activities of this invention is in the range of $1 \times 10^{-7}$ to 200 mg/kg/day, preferably $1 \times 10^{-4}$ to 100 mg/kg/day, which can be administered as a single dose or divided into multiple doses.

The formulations of this invention are preferably administered parenterally, e.g., intramuscularly, intraperitoneally, intravenously, subcutaneously, and the like.

Preparations according to this invention for parenteral administration include sterile aqueous or non-aqueous solutions, suspensions, gels, or emulsions, provided that the desired in vivo release profile is achieved. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Synthesis of Peptides

Peptides useful for practicing the present invention can be and were prepared by standard solid phase peptide synthesis. See, e.g., Stewart, J. M., et al., *Solid Phase Synthesis* (Pierce Chemical Co., 2d ed. 1984).

The following examples describe synthetic methods that can be and were used for making peptides with which the instant invention may advantageously be practiced, which synthetic methods are well-known to those skilled in the art. Other methods are also known to those skilled in the art. The examples are provided for the purpose of illustration and are not meant to limit the scope of the present invention in any manner.

Boc-βAla-OH, Boc-D-Arg(Tos)-OH and Boc-D-Asp(OcHex) were purchased from Nova Biochem, San Diego, Calif. Boc-Aun-OH was purchased from Bachem, King of Prussia, Pa. Boc-Ava-OH and Boc-Ado-OH were purchased from Chem-Impex International, Wood Dale, Ill. Boc-2Nal-OH was purchased from Synthetech, Inc. Albany, Oreg.

The full names for other abbreviations used herein are as follows: Boc for t-butyloxycarbonyl, HF for hydrogen fluoride, Fm for formyl, Xan for xanthyl, Bzl for benzyl, Tos for tosyl, DNP for 2,4-dinitrophenyl, DMF for dimethylformamide, DCM for dichloromethane, HBTU for 2-(1H-Benzotriazol-1-yl)-1,1,3,3-tetramethyl uronium hexafluorophosphate, DIEA for diisopropylethylamine, HOAc for acetic acid, TFA for trifluoroacetic acid, 2CIZ for 2-chlorobenzyloxycarbonyl, 2BrZ for 2-bromobenzyloxycarbonyl, OcHex for O-cyclohexyl, Fmoc for 9-fluorenylmethoxycarbonyl, HOBt for N-hydroxybenzotriazole; PAM resin for 4-hydroxymethylphenylacetamidomethyl resin; Tris for Tris(hydroxymethyl)aminomethane; and Bis-Tris for Bis(2-hydroxyethyl)amino-tris(hydroxymethyl)methane (i.e., 2-Bis(2-hydroxyethyl)amino-2-(hydroxymethyl)-1,3-propanediol). The term "halo" or "halogen" encompasses fluoro, chloro, bromo and iodo.

Unless defined otherwise, all technical and scientific terms used herein have the same meaning as commonly understood by one of ordinary skill in the art to which this invention belongs. Also, all publications, patent applications, patents and other references mentioned herein are incorporated by reference.

Example 1

A detailed synthesis procedure for (Aib$^{8,35}$)hGLP-1(7-36)NH$_2$ has been provided in International Patent Publication No. WO 00/34331 (PCT/EP99/09660), the contents of which are incorporated herein in their entirety. Briefly, the compound was synthesized on an Applied Biosystems (Foster City, Calif.) model 430A peptide synthesizer which was modified to do accelerated Boc-chemistry solid phase peptide synthesis. See Schnolzer, et al., Int. J. Peptide Protein Res., 90:180 (1992). 4-methylbenzhydrylamine (MBHA) resin (Peninsula, Belmont, Calif.) with the substitution of 0.91 mmol/g was used. The Boc amino acids (Bachem, Calif., Torrance, Calif.; Nova Biochem., LaJolla, Calif.) were used with the following side chain protection: Boc-Ala-OH, Boc-Arg(Tos)-OH, Boc-Asp(OcHex)-OH, Boc-Tyr(2BrZ)-OH, Boc-His(DNP)-OH, Boc-Val-OH, Boc-Leu-OH, Boc-Gly-OH, Boc-Gln-OH, Boc-Ile-OH, Boc-Lys(2CIZ)-OH, Boc-Thr(Bzl)-OH, Boc-Ser(Bzl)-OH, Boc-Phe-OH, Boc-Aib-OH, Boc-Glu(OcHex)-OH and Boc-Trp(Fm)-OH. The Boc groups were removed by treatment with 100% TFA for 2×1 min. Boc amino acids (2.5 mmol) were pre-activated with HBTU (2.0 mmol) and DIEA (1.0 mL) in 4 mL of DMF and were coupled without prior neutralization of the peptide-resin TFA salt. Coupling times were 5 min. except for the Boc-Aib-OH residues and the following residues, Boc-Lys(2CIZ)-OH and Boc-His(DNP)-OH wherein the coupling times were 2 hours.

At the end of the assembly of the peptide chain, the resin was treated with a solution of 20% mercaptoethanol/10% DIEA in DMF for 2×30 min. to remove the DNP group on the His side chain. The N-terminal Boc group was then removed by treatment with 100% TFA for 2×2 min. After neutralization of the peptide-resin with 10% DIEA in DMF (1×1 min), the formyl group on the side chain of Trp was removed by treatment with a solution of 15% ethanolamine/15% water/70% DMF for 2×30 min. The peptide-resin was washed with DMF and DCM and dried under reduced pressure. The final cleavage was done by stirring the peptide-resin in 10 mL of HF containing 1 mL of anisole and dithiothreitol (24 mg) at 0° C. for 75 min. HF was removed by a flow of nitrogen. The residue was washed with ether (6×10 mL) and extracted with 4N HOAc (6×10 mL).

The peptide mixture in the aqueous extract was purified on reverse-phase preparative high pressure liquid chromatography (HPLC) using a reverse phase VYDA® $C_{18}$ column (Nest Group, Southborough, Mass.). The column was eluted with a linear gradient (20% to 50% of solution B over 105 min.) at a flow rate of 10 ml/min (Solution A=water containing 0.1% TFA; Solution B=acetonitrile containing 0.1% of TFA). Fractions were collected and checked on analytical HPLC. Those containing pure product were combined and lyophilized to dryness. In one example of synthesis of this compound, 135 mg of a white solid was obtained. Purity was 98.6% based on analytical HPLC analysis. Electro-spray mass spectrometer (MS(ES))S analysis gave the molecular weight at 3339.7 (in agreement with the calculated molecular weight of 3339.7).

Example 2

Formulation Procedures I 2.1 Materials, Stock Solutions, Calculations
A) Materials: $ZnCl_2$, NaOH pellets, and hydrochloric acid, 35%, were obtained from Panreac Quimica, Barcelona, Spain. WFI (sterile water for injection/irrigation) was obtained from B. Braun Medical, Barcelona, Spain.
B) Stock Solutions
   (i) $ZnCl_2$, pH=3:
    1. With stirring, add 35% HCl to WFI to achieve pH=3.
    2. In a volumetric flask, transfer a weighed amount of $ZnCl_2$. With stirring, add pH=3 HCl to achieve a final concentration of approximately 1-4 mg $ZnCl_2$/mL.
   (ii) $ZnCl_2$, pH=2:
    1. With stirring, add 35% HCl to WFI to achieve pH=2.
    2. In a volumetric flask, transfer a weighed amount of $ZnCl_2$. With stirring, add pH=2 HCl to achieve a final concentration of approximately 4-12 mg $ZnCl_2$/mL.
   (iii) NaOH. 0.1 to 10 mg/ml:
    1. In a volumetric flask, transfer a weighed amount of NaOH. With stirring, add WFII to achieve a final concentration of approximately 0.1-10 mg NaOH/mL
   (iv) Freeze-dried 20 mg aliquot $(Aib^{8,35})$HGLP-1(7-36)$NH_2$/vial:
    1. Prepare a 0.04% (v/v) dilution of acetic acid and WFI.
    2. In a volumetric flask, transfer a weighed amount of $(Aib^{8,35})$HGLP-1(7-36)$NH_2$ (acetate salt). With stirring, add sufficient 0.04% acetic acid to bring the final concentration to 20 mg $(Aib^{8,35})$HGLP-1(7-36)$NH_2$/mL. Following filter sterilization using 0.45 micron filters, 1 ml aliquots of the solution were transferred to lyophilization vials, freeze dried and the dried product stored at −22° C.
   (v) Freeze-dried 50 mg aliquot $(Aib^{8,35})$HGLP-1(7-36)$NH_2$/vial:
    1. Prepare a 0.1% (v/v) dilution of acetic acid and WFI.
    2. In a volumetric flask, transfer a weighed amount of $(Aib^{8,35})$HGLP-1(7-36)$NH_2$ (acetate salt). With stirring, add sufficient 0.1% acetic acid to bring the final concentration to 50 mg $(Aib^{8,35})$HGLP-1(7-36)$NH_2$/mL. Following filter sterilization, 1 ml aliquots of the solution are transferred to lyophilization vials and freeze dried.
C) Calculations
   (i) To determine the total weight/volume of excipient (E) for a composition:

$$E=(A\times 100/T)-(A/P)$$

wherein:
   E=excipient in mg
   A=content of pure peptide (mg);
   T=target concentration of the composition; e.g., 2 if target is 2%; and
   P=concentration of pure peptide (mg peptide/100 mg formulation)

With respect to the total volume of excipient, the assumption that 1 mL=1 g is applied.
   (ii) To determine the volume/weight (W) of $ZnCl_2$ to add to each ml or g of composition solution:
    a) W=100% E for compositions in which no pH adjustment is made;
    b) W=80% E for liquid formulations in which the peptide is about 1%, or about 2% or up to about 10% and the pH is adjusted using a base;
    c) W=50% E for semi-solid or gel formulations in which the peptide is about 1%, or about 2% or up to about 10% and the pH is adjusted using a base;
    d) W=66.66% E for semi-solid or gel formulations in which the peptide is about 25% and the pH is adjusted using a base;
    e) W=90% E for formulations in which the peptide is reconstituted from a freeze-dried preparation and the pH is adjusted using a base.
   (iii) To determine the volume/weight (W) of NaOH to add to each ml or g of composition solution:
    a) W=20% E for formulations in which the peptide is about 1%, or about 2% or up to about 10% and the pH is adjusted using a base;
    b) W=50% E for semi-solid or gel formulations in which the peptide is about 1%, or about 2% or up to about 10% and the pH is adjusted using a base;
    c) W=33.33% E for semi-solid or gel formulations in which the peptide is about 25% and the pH is adjusted using a base;
    d) W=10% E for formulations in which the peptide is reconstituted from a freeze-dried preparation and the pH is adjusted using a base.
   (iv). To determine the concentration of $ZnCl_2$ (mg/ml or mg/g) to be used in each composition:

$$[ZnCl_2]=(136.29\times A)/(W\times 3339.76\times R)$$

wherein:
   A=content of pure peptide (mg).
   R=molar ratio of peptide/Zn
   R=1.5 for formulations in which the peptide is about 1%, or about 2% or about 10% or up to about 23%;
   R=4.0 formulations in which the peptide is about 25%; and
   W=weight (g) or volume (mL) of $ZnCl_2$ solution to add to each g or ml of composition solution.

2.2 Preparation of Compositions with 1-10% Freeze-Dried Peptide and $ZnCl_2$, No pH Adjustment As used herein, a formulation comprising a percentage of peptide describes a formulation comprising a weight of peptide per total weight of the composition, e.g., 1% peptide, describes a formulation comprising 1 g of peptide per 10 g of total composition. Formulations comprising about 1%, or about 2% up to about 10% peptide were prepared as follows. Freeze-dried samples of $(Aib^{8,35})$HGLP-1(7-36)$NH_2$ prepared as described were thoroughly mixed with a $ZnCl_2$ stock solution pH 3 at 100% of the total excipient volume and [peptide:Zn]=1.5:1.

A) 1% compositions are prepared by mixing 20 mg freeze-dried (Aib$^{8,35}$)HGLP-1(7-36)NH$_2$ (see 2.1 B (iv) above) with 2 ml of ZnCl$_2$ solution (0.272 mg/ml; see 2.1 B (i) above)

B) 2% compositions are prepared by mixing 20 mg freeze-dried (Aib$^{8,35}$)HGLP-1(7-36)NH$_2$ (see 2.1 B (iv) above) with 1 ml of ZnCl$_2$ solution (0.544 mg/ml; see 2.1 B (i) above)

C) 10% compositions are prepared by mixing 50 mg freeze-dried (Aib$^{8,35}$)HGLP-1(7-36)NH$_2$ (see 2.1 B (v) above) with 0.45 ml of ZnCl$_2$ solution (3.023 mg/ml; see 2.1 B (i) above)

Freeze-dried peptides and solutions were allowed to equilibrate to room temperature. The designated volume of ZnCl$_2$ solution was injected into the vial containing the freeze-dried peptide and hydration allowed to proceed for about 2 minutes for 1% or 2% peptide compositions to about 60 minutes for 10% peptide composition, or until all freeze-dried peptide is completely hydrated and the solution is free of clumps of peptide. Following hydration, the reconstituted peptide is shaken for approximately 1 minute.

The appropriate amount of dissolved peptide may be removed for dosing, e.g., 100 ul of a 1% peptide solution prepared as per A above equates to a 1 mg dose, 50 ul of a 2% peptide solution prepared as per B above equates to a 1 mg dose, 150 ul of a 10% peptide solution prepared as per C above equates to a 15 mg dose, etc.

Using the teachings of the instant application, one skilled in the art could vary the amounts of peptide and ZnCl$_2$ to achieve compositions other than the 1%, 2% and 10% compositions detailed below as well as desired dosages.

2.3 Preparation of Compositions with 1-10% Freeze-Dried Peptide and ZnCl$_2$, with a pH Adjustment Formulations comprising about 1%, or about 2% up to about 10% peptide were prepared as follows. Freeze-dried samples of (Aib$^{8,35}$)HGLP-1(7-36)NH$_2$ prepared as described were thoroughly mixed with a ZnCl$_2$ stock solution pH 3 at 90% of the total excipient volume. The desired pH of the solution is reached by the addition of diluted NaOH solution.

A) 1% compositions are prepared by mixing 20 mg freeze-dried (Aib$^{8,35}$)HGLP-1(7-36)NH$_2$ (see 2.1 B (iv) above) with 1.8 ml of ZnCl$_2$ solution (see 2.1 B (i) above)

B) 2% compositions are prepared by mixing 20 mg freeze-dried (Aib$^{8,35}$)HGLP-1(7-36)NH$_2$ (see 2.1 B (iv) above) with 0.9 ml of ZnCl$_2$ solution (see 2.1 B (i) above)

C) 10% compositions are prepared by mixing 50 mg freeze-dried (Aib$^{8,35}$)HGLP-1(7-36)NH$_2$ (see 2.1 B (v) above) with 0.40 ml of ZnCl$_2$ solution (see 2.1 B (i) above)

To the above solutions, add the necessary volume (10% of total volume of excipient) of diluted NaOH solution to achieve the target concentration and pH. For example, to each:

1% composition: Add 0.2 mL of NaOH solution of proper concentration

2% composition: Add 0.1 mL of NaOH solution of proper concentration

10% composition: Add 0.05 mL of NaOH solution of proper concentration

Using the teachings of the instant application, one skilled in the art could vary the amounts of peptide and ZnCl$_2$ to achieve compositions other than the 1%, 2% and 10% compositions detailed below.

2.4 Preparation of Liquid Compositions with 1-10% Peptide and ZnCl$_2$, No pH Adjustment Liquid formulations comprising about 1%, or about 2% up to about 10% peptide were prepared as follows. Samples of (Aib$^{8,35}$)HGLP-1(7-36)NH$_2$ were weighed and mixed with a ZnCl$_2$ stock solution pH 3 to achieve the target concentration of 1%, 2%, up to 10% peptide. Following mixing, the composition is filter sterilized and stored until use.

2.5 Preparation of Liquid Compositions with 1-10% Peptide and ZnCl$_2$, pH Adjustment Liquid formulations comprising about 1%, or about 2% up to about 10% peptide were prepared as follows. Samples of (Aib$^{8,35}$)HGLP-1(7-36)NH$_2$ were weighed and thoroughly mixed with a ZnCl$_2$ stock solution pH 3 at 80% of the total excipient volume. The zinc solution may be either ZnCl$_2$ or ZnAc2.2H2O. The desired pH of the solution is reached by the addition of diluted NaOH solution. Preparations C5 to C13 were prepared using this method.

Using the teachings of the instant application, one skilled in the art could vary the amounts of peptide and ZnCl$_2$ to achieve compositions other than the 1%, 2% and 10% described herein.

2.6 Preparation of Semi-Solid/Gel Compositions with 25% Peptide and ZnCl$_2$, No pH Adjustment Semi-solid or gel formulations comprising about 25% peptide were prepared as follows. Samples of (Aib$^{8,35}$)HGLP-1(7-36)NH$_2$ were weighed and thoroughly mixed with a ZnCl$_2$ stock solution pH 2 at 66.66% of the total excipient volume. The zinc solution may be either ZnCl$_2$ or ZnAc$_2$.2H$_2$O. Preparations C1 and C2 were prepared using this method.

Figure 4:
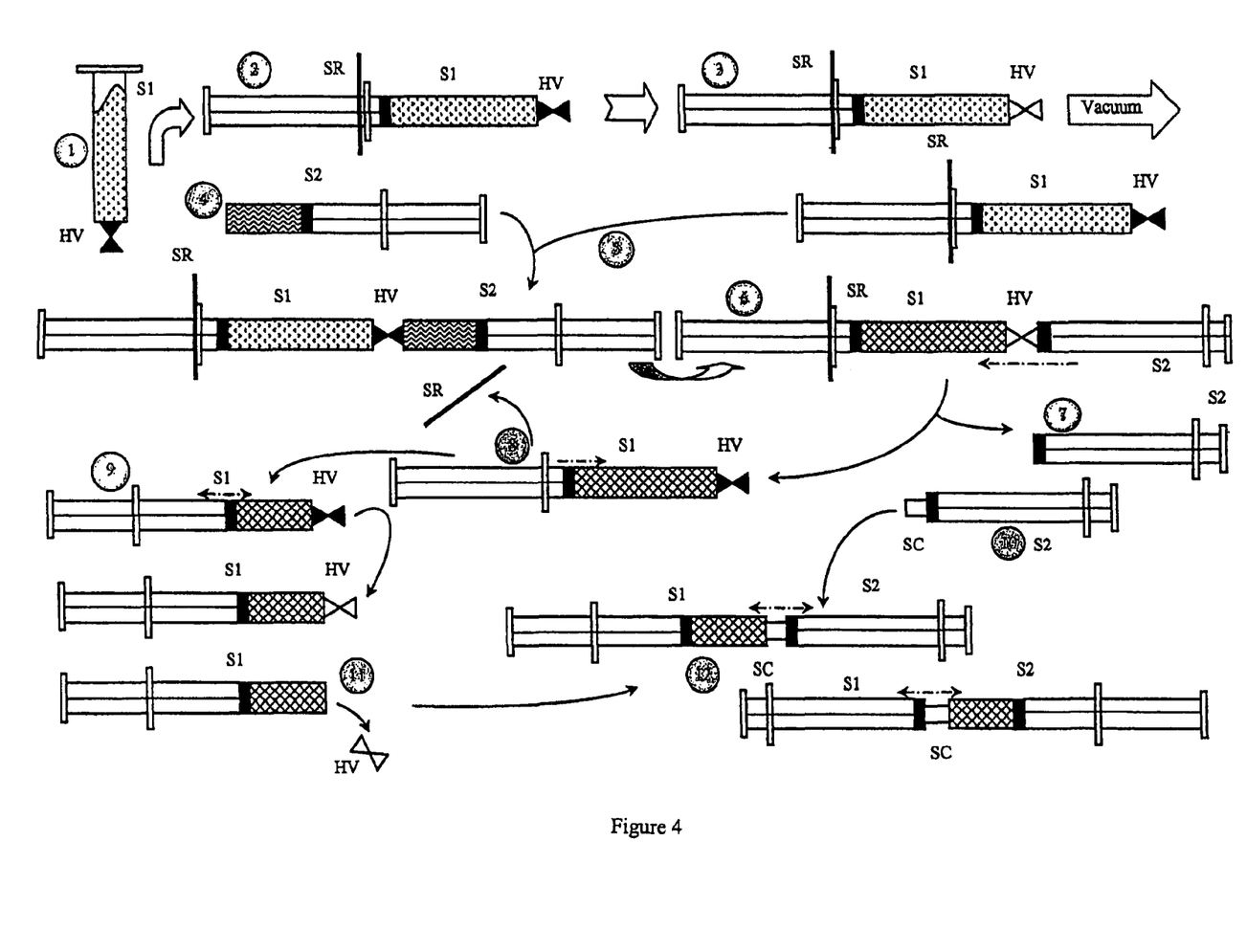
FIG. 4 provides a schematic presentation of various devices useful in preparing certain formulations of the present invention.

More specifically, the semi-solid or gel compositions were prepared using a "push-pull" mixing method:

a) The desired amount of peptide was weighed into the barrel of a disposable syringe S1 previously fitted with a special two-way hand valve HV (I.D.=0.5 mm) and tubing was placed inside the syringe Luer hole;

b) The syringe plunger was secured with a stainless steel rod SR;

c) HV in S1 was connected to a vacuum source and HV was opened. After 10 min HV was closed;

d) The Zinc solution was accurately weighed into the barrel of a second disposable syringe S2;

e) S2 was then connected to the free part of HV;

f) HV was opened and the solvent was pulled by the vacuum into the barrel containing the peptide powder S1;

g) HV was closed and the solvent syringe S2 was removed, thus hydrating the peptide powder in S1;

h) SR was removed and the syringe plunger was slowly released;

i) The syringe plunger is moved (push and pull), without opening HV, so that the powder mass is fully soaked by solvent;

j) A two-way stainless connector SC (I.D.=1.0 mm) was placed in syringe S2 with the tubing placed inside the syringe Luer hole, and its plunger was pushed to the end;

k) HV in S1 was opened to vent the vacuum and then HV was removed. The syringe plunger was moved so that air in the syringe barrel was minimized; and l) S1 and S2 were connected by SC and the composition was kneaded from S1 to S2 through SC.

Using the teachings of the instant application, one skilled in the art could vary the amounts of peptide and ZnCl$_2$ to achieve compositions other than the 25% described herein.

2.7 Preparation of Semi-Solid/Gel Compositions with 25% Peptide and ZnCl$_2$, pH Adjustment Semi-solid or gel formulations comprising about 25% peptide were prepared as follows. Samples of (Aib$^{8,35}$)HGLP-1(7-36)NH$_2$ were weighed and thoroughly mixed with a ZnCl$_2$ stock solution pH 2 at 66.66% of the total excipient volume. The zinc solution may be either ZnCl$_2$ or ZnAc$_2$.2H$_2$O. The desired pH of the solution is reached by the addition of diluted NaOH solution. In this example, the total volume of liquid added to the powder must be divided between the zinc and the NaOH solutions. Therefore, the concentration of the zinc solution was adjusted so that the total volume of zinc solution needed was reduced to 50% of the total liquid volume added to the peptide powder (step d). The remaining 50% of the total liquid volume added to the peptide powder was added as NaOH solution as detailed below. Preparations C3 and C4 were prepared using this method.

The pH adjusted semi-solid or gel compositions were prepared using a "push-pull" mixing method:

a) The desired amount of peptide was weighed into the barrel of a disposable syringe S1 previously fitted with a special two-way hand valve HV (I.D.=0.5 mm) and tubing was placed inside the syringe Luer hole;

b) The syringe plunger was secured with a stainless steel rod SR;

c) HV in S1 was connected to a vacuum source and HV was opened. After 10 min HV was closed;

d) The Zinc solution was accurately weighed into the barrel of a second disposable syringe S2;

e) S2 was then connected to the free part of HV;

f) HV was opened and the solvent was pulled by the vacuum into the barrel containing the peptide powder S1;

g) HV was closed and the solvent syringe S2 was removed, thus hydrating the peptide powder in S1;

h) SR was removed and the syringe plunger was slowly released;

i) The syringe plunger is moved (push and pull), without opening HV, so that the powder mass is fully soaked by solvent;

j) A two-way stainless connector SC (I.D.=1.0 mm) was placed in syringe S2 with the tubing placed inside the syringe Luer hole, and its plunger was pushed to the end;

k) HV in S1 was opened to vent the vacuum and then HV was removed. The syringe plunger was moved so that air in the syringe barrel was minimized;

l) S1 and S2 were connected by SC and the composition was kneaded from S1 to S2 through SC;

m) After homogenization, an aliquot of the mixed product was removed to determine the concentration of the peptide;

n) The remaining intermediate bulk product was accurately weighed and the amount of NaOH solution required to reach the desired pH was calculated;

o) The NaOH solution was accurately weighed into a third disposable syringe S3; and p) The syringe plungers were slowly compressed to minimize the air in the syringe chambers. Both syringes were connected by SC and the composition was kneaded through SC.

Using the teachings of the instant application, one skilled in the art could vary the amounts of peptide and $ZnCl_2$ to achieve compositions other than the 25% described herein.

TABLE 1

| Ex. No. | *Peptide % | Solution | **Peptide: Zn Ratio | Peptide Dose |
|---|---|---|---|---|
| C1 | 10 | $ZnCl_2$ 0.846 mg/ml | 5.4:1 | 1 mg |
| C2 | 5 | 0.40 mg $ZnCl_2$/mL | 5.4:1 | 1 mg |
| C3 | 10 | 50% $ZnCl_2$ 1.69 mg/mL, 50% NaOH 1 mg/mL | 5.4:1 | 1 mg |
| C4 | 10 | 50% $ZnCl_2$ 2.28 mg/mL, 50% NaOH 1 mg/mL | 4:1 | 1 mg |
| C5 | 5 | 80% $ZnCl_2$ 0.674 mg/mL, 20% NaOH 3.81 mg/mL | 4:1 | 1 mg |
| C6 | 2 | 80% $ZnCl_2$ 0.26 mg/mL, 20% NaOH 2.15 mg/mL | 5.4:1 | 1 mg |
| C7 | 10 | 80% $ZnCl_2$ 3.81 mg/mL, 20% NaOH 4.47 mg/mL | 1.5:1 | 1 mg |
| C8 | 10 | 80% $ZnAc_2.2H_2O$ 2.3 mg/mL, 20% NaOH 6.1 mg/mL | 4:1 | 1 mg |
| C9 | 2 | 80% $ZnCl_2$ 0.695 mg/mL, 20% NaOH 1.75 mg/mL | 1.5:1 | 1 mg |
| C10 | 2 | 80% $ZnAc_2.2H_2O$ 1.12 mg/mL, 20% NaOH 1.44 mg/mL | 1.5:1 | 1 mg |
| C11 | 2 | 80% $ZnCl_2$ 0.695 mg/mL, 20% NaOH 1.75 mg/mL | 1.5:1 | 1 mg |
| C12 | 1 | 80% $ZnCl_2$ 0.384 mg/mL, 20% NaOH 0.875 mg/mL | 1.5:1 | 1 mg |
| C13 | 10 | 80% $ZnCl_2$ 3.85 mg/mL, 20% NaOH 4.47 mg/mL | 1.5:1 | 15 mg |

*Target value shown. Actual value was within 5% of target in all cases
**Target value shown. Actual values were within 10% of target in all cases 3.0 Determination of GLP-1 Receptor Affinity A compound useful to practice the present invention can be tested for its ability to bind to the GLP-1 receptor using the following procedure.

Cell Culture:

RIN 5F rat insulinoma cells (ATCC-# CRL-2058, American Type Culture Collection, Manassas, Va.), expressing the GLP-1 receptor, were cultured in Dulbecco's modified Eagle's medium (DMEM) containing 10% fetal calf serum, and maintained at about 37° C. in a humidified atmosphere of 5% $CO_2$/95% air.

Radioligand Binding:

Membranes were prepared for radioligand binding studies by homogenization of the RIN cells in 20 ml of ice-cold 50 mM Tris-HCl with a Brinkman Polytron (Westbury, N.Y.) (setting 6, 15 sec). The homogenates were washed twice by centrifugation (39,000 g/10 min), and the final pellets were resuspended in 50 mM Tris-HCl, containing 2.5 mM $MgCl_2$, 0.1 mg/ml bacitracin (Sigma Chemical, St. Louis, Mo.), and 0.1% BSA. For assay, aliquots (0.4 ml) were incubated with 0.05 nM ($^{125}$I)GLP-1(7-36) (~2200 Ci/mmol, New England Nuclear, Boston, Mass.), with and without 0.05 ml of unlabeled competing test peptides. After a 100 min incubation (25° C.), the bound ($^{125}$I)GLP-1(7-36) was separated from the free by rapid filtration through GF/C filters (Brandel, Gaithersburg, Md.), which had been previously soaked in 0.5% polyethyleneimine. The filters were then washed three times with 5 ml aliquots of ice-cold 50 mM Tris-HCl, and the bound radioactivity trapped on the filters was counted by gamma spectrometry (Wallac LKB, Gaithersburg, Md.). Specific binding was defined as the total ($^{125}$I)GLP-1(7-36) bound minus that bound in the presence of 1000 nM GLP1 (7-36) (Bachem, Torrence, Calif.).

4. Determination of Solubility vs pH 4.1. Determination of Compound Solubility vs pH in Buffered Saline A compound that may advantageously be used to practice the invention can be tested to determine its solubility in PBS at different pHs and temperatures using the following procedure.

A stock PBS buffered solution is made by dissolving one packet of pre-mixed powder (SIGMA, Product No.: P-3813) in one liter of de-ionized water to yield 10 mM phosphate-buffered saline with 138 mM NaCl, 2.7 mM KCl, and a pH of 7.4. PBS buffers with different pH values may be made by adjusting the pH of this stock solution with phosphoric acid and/or sodium hydroxide.

Two mg samples of a compound to be tested, e.g., 2 mg of a compound of Example 1, may be weighed into glass vials. Into each vial is added a 50 µl aliquot of PBS buffer at a certain pH. The solution is vortexed, and if necessary sonicated, until clear. For each pH tested the total volume of buffer needed to dissolve 2 mg of the compound is recorded and the solubility was calculated.

Peptide solutions that are clear at room temperature (20-25° C.) are placed in a refrigerator (4° C.) overnight and the solubility of the peptide at 4° C. is then examined.

4.2. Determination of Compound Solubility vs pH in Saline

A compound that may advantageously be used to practice the invention can be tested to determine its solubility in saline at different pH values and temperatures using the following procedure.

A stock saline solution is prepared by dissolving 9 grams of NaCl in one liter of de-ionized water. Saline solutions with different pH values are made by adjusting the pH of this stock solution with HCl and/or NaOH.

Two mg samples of a compound to be tested, e.g., 2 mg of a compound of example 1, are weighed into glass vials. Into each vial is added a 50 µl aliquot of saline solution at a certain pH. The vial is vortexed and, if necessary, sonicated until clear. For each tested pH the total volume of saline needed to dissolve 2 mg of the compound is recorded and the solubility is calculated.

Solutions that are clear at room temperature (20-25° C.) are placed in a refrigerator (4° C.) overnight and the solubility at 4° C. then examined.

4.3. Determination of Compound Solubility in Saline at pH 7.0

Compounds that may advantageously be used to practice the invention can be tested to determine their solubility at room temperature in saline having pH=7 using the following procedure.

Saline solution is prepared by dissolving 9 grams of NaCl in one liter of de-ionized water. A 2 mg sample of a compound to be tested, e.g., a compound of example 1, is weighed into a glass vial and 1 mL aliquots of saline are added, with vortexing and sonication, until clear. The total volume of saline used to dissolve 2 mg of peptide is recorded and the solubility at room temperature is calculated.

4.4. Determination of Compound Solubility in Saline at Various pH

Compounds that may advantageously be used to practice the invention can be tested to determine their solubility at room temperature in saline solutions having various pH values using the following procedure.

A stock saline solution is prepared by dissolving 9 grams of NaCl in one liter of de-ionized water. Saline solutions having various pH values are obtained by treating aliquots of this stock saline solution with HCl and NaOH.

A 2 mg sample of a compound to be tested, e.g., the compound of example 1, is weighed into a glass vial. Aliquots of 50 µl of a saline buffer at a certain pH are added. The solution is vortexed and sonicated until clear. The total volume of buffer used to dissolve 2 mg of peptide is recorded and the solubility is calculated.

5. Determination of Aqueous Solubility of Compound vs Zinc Concentration

A compound that may advantageously be used to practice the invention can be tested to determine its solubility in pH 7 water at different zinc concentrations using the following procedure.

A stock zinc solution is prepared by dissolving $ZnCl_2$ in de-ionized water to a concentration of 100 mg/ml and adjusting the pH to 2.7 using HCl. Solutions having various $ZnCl_2$ concentrations ("Zn Test Solutions") are prepared by making appropriate dilutions of the stock solution.

One mg of a compound to be tested, e.g., 1 mg of the compound of example 1, is dissolved in 250 µl of each Zn Test Solution to yield a solution having 4 mg/ml of the compound. The pH of this solution is then adjusted using 0.2 N NaOH until white precipitates are observed to form. The precipitation solution was centrifuged and the mother liquor analyzed using HPLC. The UV absorption area of test compound peak is measured and the concentration of the test compound in the mother liquor is determined via comparison to a calibration curve.

As a representative example of a compound that may be used to practice the invention, the compound of Example 1 was tested in the immediately foregoing assay and the following results were obtained (aqueous saline, pH 7.0, room temperature):

TABLE 2

| $ZnCl_2$ concentration (µg/mL) | Solubility (mg/mL) |
|---|---|
| 0 | 5.788 |
| 80 | 0.0770 |
| 500 | 0.0579 |
| 1000 | 0.0487 |
| 1500 | 0.0668 |
| 2500 | 0.1131 |

6. Determination of pI using IEF gels

Invitrogen's Novex IEF pH3-10 gels may be used to measure the pI of GLP-1 peptides. Peptidyl compounds to be tested are dissolved in water to a concentration of 0.5 mg/ml. For each such compound, 5 µl of the resulting solution is mixed with 5 µl of Novex® Sample Buffer 2× (comprised of 20 mM Arginine free base, 20 mM Lysine free base and 15% Glycerol) and the resulting 10 µl sample solution is loaded onto the gel along with a protein standard sample.

Running buffers are also obtained from Invitrogen and the gel is run according to manufacture's instructions, generally as follows: 100 V constant for 1 hour, followed by 200 V constant for 1 hour, followed by 500 V constant for 30 minutes.

The gel is then fixed in 12% TCA containing 3.5% sulfosalicylic acid for 30 minutes, and then stained for 2 hours with Colloidal Coomassie Blue according to the instructions found on the Novex® Colloidal Blue Kit thereafter, then de-stained in water overnight.

The gel is scanned and analyzed by the program Fragment Analysis 1.2. pI's of unknown peptides are calculated relative to the pI's of standard compounds having pI values of: 10.7, 9.5, 8.3, 8.0, 7.8, 7.4, 6.9, 6.0, 5.3, 5.2, 4.5, 4.2, and 3.5.

7. In Vivo Assays in Rat

Compositions of the present invention can be tested to determine their ability to promote and enhanced effect in vivo using the following assays.

7.1. Experimental Procedure:

The day prior to the experiment, adult male Sprague-Dawley rats (Taconic, Germantown, N.Y.) that weighed approximately 300-350 g were implanted with a right atrial jugular cannula under chlorohydrate anesthetic. The rats were then fasted for 18 hours prior to the injection of the appropriate test composition or vehicle control at time 0. The rats continued to be fasted throughout the entire experiment.

A 0.5 mg/ml $ZnCl_2$ solution was prepared by dilution of a solution of 100 mg/ml $ZnCl_2$ in an HCl solution having pH 2.7 water. 1 mg of the compound of formula (I) ((Aib$^{8,35}$)

hGLP1(7-36)NH$_2$) was dissolved in 250 µl of this solution to yield a clear solution having 4 mg/ml of the compound and 0.5 mg/ml Zn at pH 4.

At time zero the rats were injected subcutaneously (sc) either with (a) the immediately forgoing solution of (Aib$^{8,35}$) hGLP-1(7-36)NH$_2$), or with vehicle control. In both cases the injection volume was very small (4-6 µL) and the dose of GLP-1 compound administered to the subject was 75 µg/kg. At the appropriate time after the sc injections a 500 µl blood sample was withdrawn via the intravenous (iv) cannula and the rats were given an iv glucose challenge to test for the presence of enhanced insulin secretion. The times of the glucose challenge were 0.25, 1, 6, 12 and 24 hours post-compound injection. After the initial blood sample was withdrawn glucose (1 g/kg) was injected iv and flushed in with 500 µl heparinized saline (10 U/mL). Thereafter, 500 µl blood samples were withdrawn at 2.5, 5, 10 and 20 minutes post-glucose injection. Each of these was immediately followed by an iv injection of 500 µl heparinized saline (10 U/mL) through the cannula. The blood samples were centrifuged, plasma was collected from each sample and the samples were stored at −20° C. until they were assayed for insulin content. The amount of insulin in each sample was determined using a rat insulin enzyme-linked immunosorbant assay (ELISA) kit (American Laboratory Products Co., Windham, N.H.).

7.1.1. Results:

A sustained insulin-enhancing activity was observed that was inducible by glucose injection over the full 24 hours of the experiment.

8. In Vivo Assays in Dog

There are a number of in vivo assays known in the art which enable the skilled artisan to determine a composition's ability to promote extended release of active compound in vivo.

8.1. 1% Peptide Composition:

By way of example, an aqueous test formulation was prepared comprising 1% (w/w) of the compound of formula (I) in a buffered solution of ZnCl$_2$ (peptide:Zn ratio=1.5:1.0).

A total of 6 male Beagle dogs, ages 42-78 months and 14-21 kg bodyweight were maintained with free access to water and once daily food (approx. 400 g of dry standard diet (SAFE 125). The dogs were fasted 18 hours before administration of test composition.

The test composition was administered by subcutaneous route in the interscapular area by. The volume of administration (approx. 20 microliters per animal) was made by 0.3 mL Terumo syringes with 0.33-12 mm (BS=30M2913). A theoretical dose of approximately 0.2 mg peptide was thus achieved.

Blood samples were taken periodically, at approx. time=0, 8, 15, 30, 45 min, and 1, 2, 4, 8, and 12 hours, and 1, 2, 3, 4, 5, and 6 days after administration. The blood was rapidly chilled after sampling until centrifugation, and the plasma decanted and rapidly frozen pending assay. Determination of peptide plasma concentration was made after off line solid phase extraction, followed by on-line phase extraction coupled to LC-MS/MS, and the data obtained managed by Analyst v1.2 software.

The composition demonstrated an extended release of the active peptide for at least 2 days.

8.2. 1% (Aib$^{8,35}$)hGLP1(7-36)NH$_2$) Solution:

Using substantially the same in vivo assay procedure as described in section 8.1, above, the following compositions were examined for their ability to release the subject peptide over an extended period of time. For each of the following four compositions the concentration of peptide was about 1% (wt/wt), the ratio of peptide to zinc was about 1.5:1, and the dose of peptide administered was approximately 1 mg.

Solution 8.2.A: (Aib$^{8,35}$)hGLP1(7-36)NH$_2$ in a solution containing (i) 90% ZnCl$_2$ (0.298 mg/mL) and (ii) 10% NaOH (0.975 mg/mL);

Solution 8.2.B: (Aib$^{8,35}$)hGLP1(7-36)NH$_2$ in a solution of ZnCl$_2$ (0.286 mg/mL)

Figure 1:
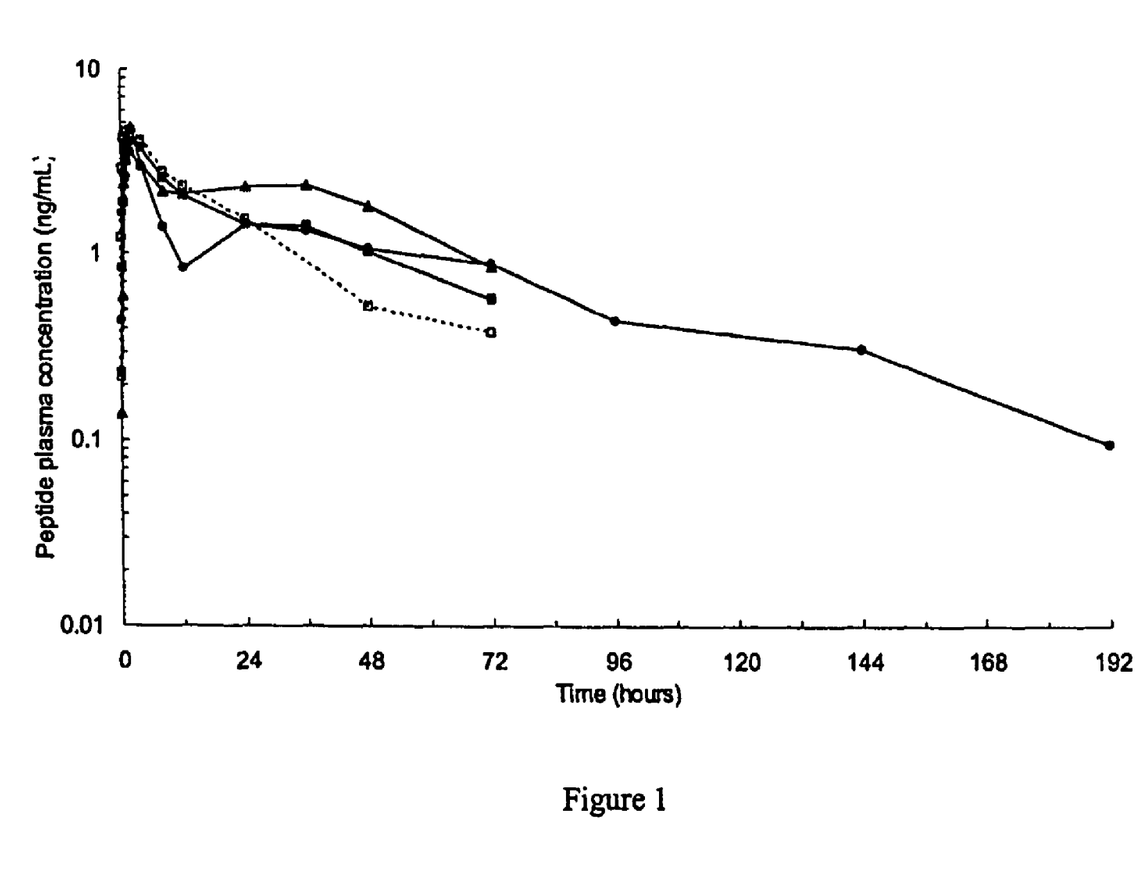
FIG. 1 depicts the plasma profiles (median values) obtained after a single subcutaneous (s.c.) administration to dogs of approximately 1 mg of [Aib$^{8,35}$]hGLP-1(7-36)NH$_2$. In each case the peptide was administered as an aqueous zinc composition comprising approximately 1% (wt/vol) peptide and having a peptide:Zn molar ratio of approximately 1.5. Filled squares and open squares represent compositions in which the pH is adjusted with NaOH as described herein; filled triangles represent a composition in which the pH was not adjusted with NaOH; filled circles represent a composition in buffered with AcOH/AcO—.

Solution 8.2.C: Substantially similar to Solution 8.2.B, and buffered using AcOH/AcO$^-$ Solution 8.2.D: Substantially similar to Solution 8.2.A The compositions provided for an extended release of (Aib$^{8,35}$)hGLP1(7-36)NH$_2$, as depicted in FIG. 1.

8.3. 1% (Aib$^{8,35}$)hGLP1(7-36)NH$_2$) Solution:

Using substantially the same in vivo assay procedure as described in section 8.1, above, the following composition was examined for its ability to release the subject peptide over an extended period of time. For the following composition the concentration of peptide was about 2% (wt/wt), the ratio of peptide to zinc was about 1.5:1, and the dose of peptide administered was approximately 1 mg.

Figure 5:
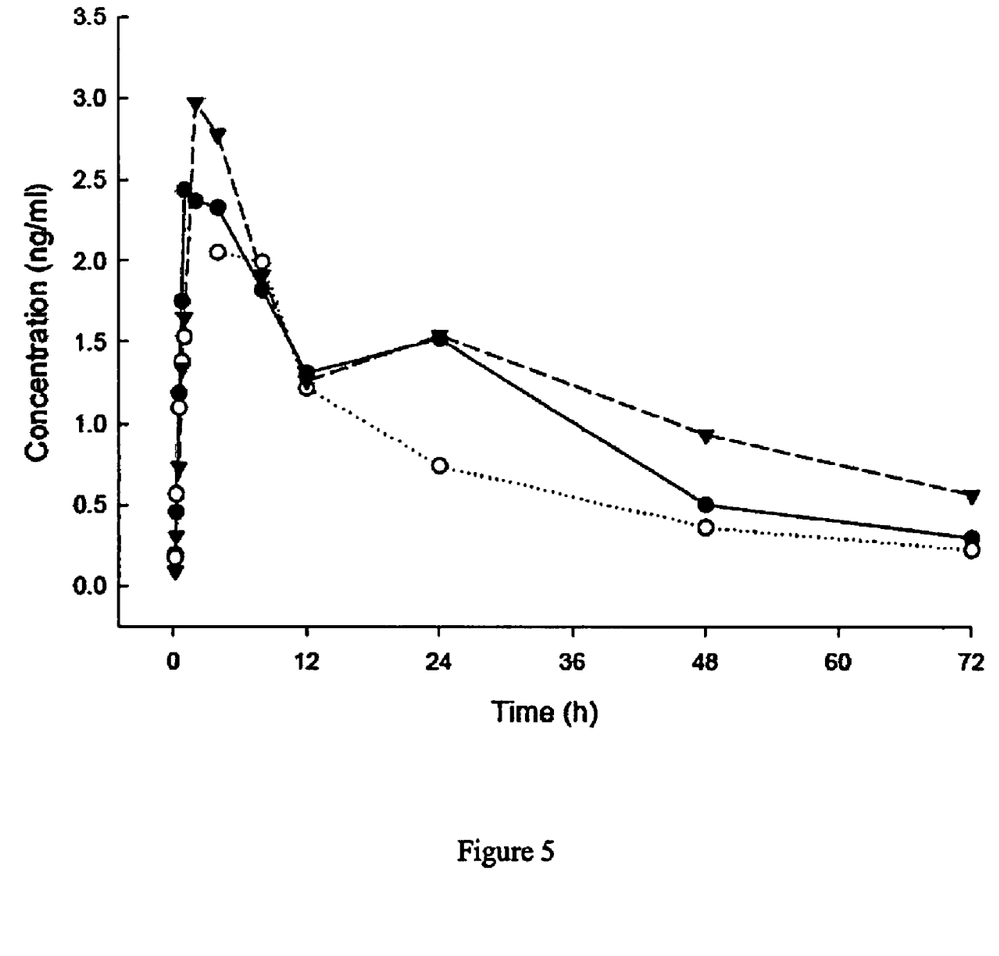
FIG. 5 depicts the plasma profiles (median values) obtained after a single subcutaneous (s.c.) administration to dogs of approximately 1 mg of [Aib$^{8,35}$]hGLP-1(7-36)NH$_2$. The peptide was administered as an aqueous zinc composition having a peptide concentration of about 2%, and a peptide:Zn molar ratio of about 1.5:1.

Solution 8.3: (Aib$^{8,35}$)hGLP1(7-36)NH$_2$ in a solution containing (i) 80% ZnCl$_2$ (0.695 mg/mL) and (ii) 20% NaOH (1.75 mg/mL);

The composition provided for an extended release of (Aib$^{8,35}$)hGLP1(7-36)NH$_2$, as depicted in FIG. 5.

8.4. 10% Peptide Solutions:

Using substantially the same in vivo assay procedure as described in section 8.1, above, the following compositions were examined for their ability to release the subject peptide over an extended period of time. For each of the following four compositions the concentration of peptide was about 10% (wt/wt), the ratio of peptide to zinc was about 1.5:1, and the dose of peptide administered was approximately 15 mg.

Solution 8.4.A: (Aib$^{8,35}$)hGLP1(7-36)NH$_2$ in a solution containing (i) 90% ZnCl$_2$ (3.367 mg/mL) and (ii) 10% NaOH (5.01 mg/mL);

Solution 8.4.B: (Aib$^{8,35}$)hGLP1(7-36)NH$_2$ in a solution of ZnCl$_2$ (2.993 mg/mL)

Figure 2:
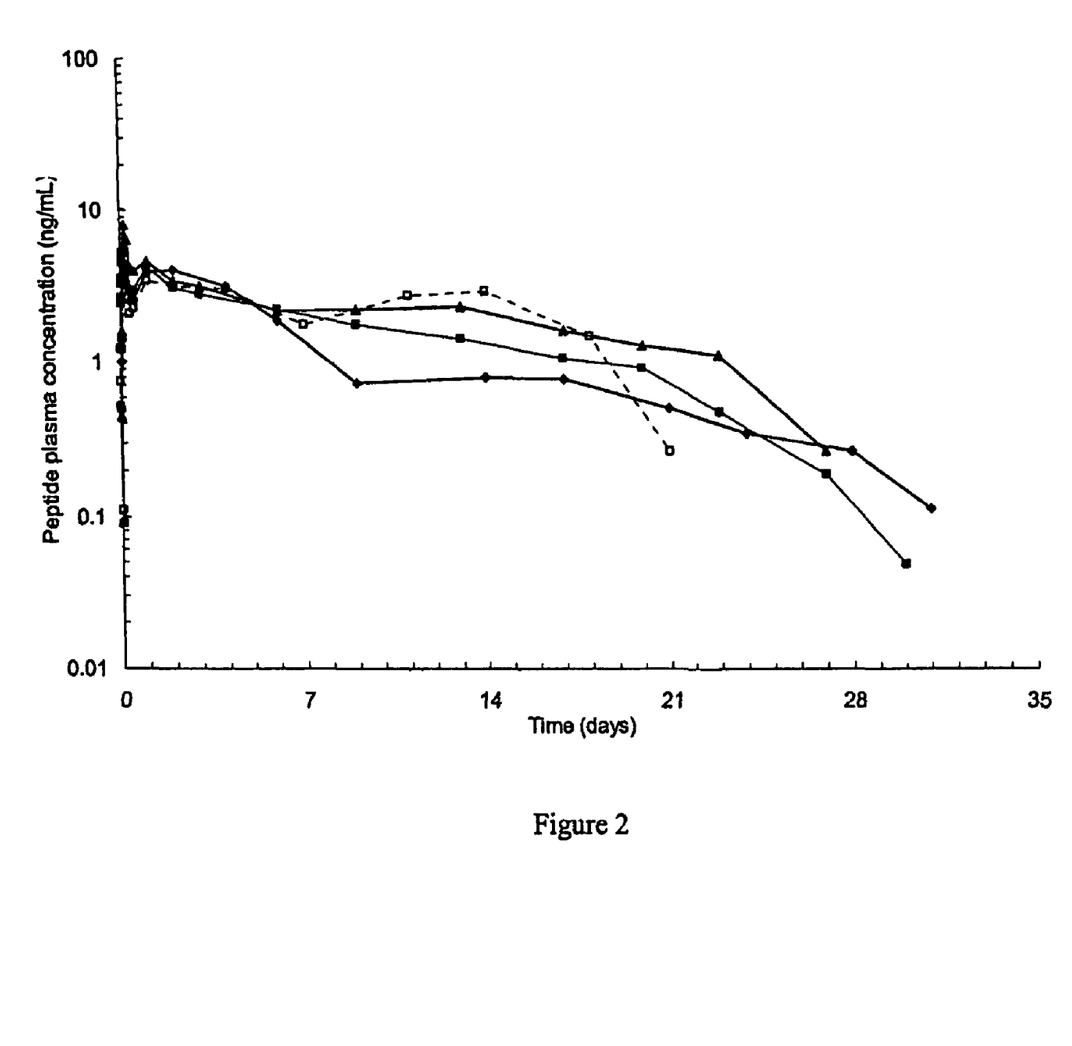
FIG. 2 depicts the plasma profiles (median values) obtained after a single subcutaneous (s.c.) administration to dogs of approximately 15 mg of [Aib$^{8,35}$]hGLP-1(7-36)NH$_2$. In each case the peptide was administered as an aqueous zinc composition comprising approximately 10% (wt/vol) peptide and having a peptide:Zn molar ratio of approximately 1.5. Filled squares and open squares represent compositions in which the pH is adjusted with NaOH as described herein; filled triangles represent a composition in which the pH was not adjusted with NaOH; filled circles represent a composition in buffered with AcOH/AcO—.

Solution 8.4.C: Substantially similar to Solution 8.4.B, and buffered using AcOH/AcO$^-$ Solution 8.4.D: Substantially similar to Solution 8.4.A The compositions provided for an extended release of (Aib$^{8,35}$)hGLP1(7-36)NH$_2$, as depicted in FIG. 2.

8.5. Semisolid Compositions:

Using substantially the same in vivo assay procedure as described in section 8.1, above, the following semi-solid compositions were examined for their ability to release the subject peptide over an extended period of time. For composition 8.5.A., the concentration of the peptide was about 5%, while for compositions 8.5.B, 8.4.C, and 8.5.D., the concentration of peptide was about 10% (wt/wt). The ratio of peptide to zinc for compositions 8.5.A, 8.5.B, and 8.5.C was about 5.4:1, while for composition 8.5.D the ratio was about 4.0:1. For all four compositions the dose of peptide administered was approximately 1 mg.

Composition 8.5.A: (Aib$^{8,35}$)hGLP1(7-36)NH$_2$ in a semi-solid composition containing ZnCl$_2$ (0.40 mg/mL) in WFI.

Composition 8.5.B: Substantially similar to Composition 8.5.A., wherein the ZnCL2 concentration has been adjusted upward to maintain a peptide:Zn ratio of about 5.4:1.

Composition 8.5.C: (Aib$^{8,35}$)hGLP1(7-36)NH$_2$ in a semi-solid containing (i) 50% ZnCl$_2$ (1.69 mg/ml) and (ii) 50% NaOH (1 mg/mL).

Composition 8.5.D: (Aib$^{8,35}$)hGLP1(7-36)NH$_2$ in a semi-solid containing (i) 50% ZnCl$_2$ (2.28 mg/ml) and (ii) 50% NaOH (1 mg/mL).

Figure 3:
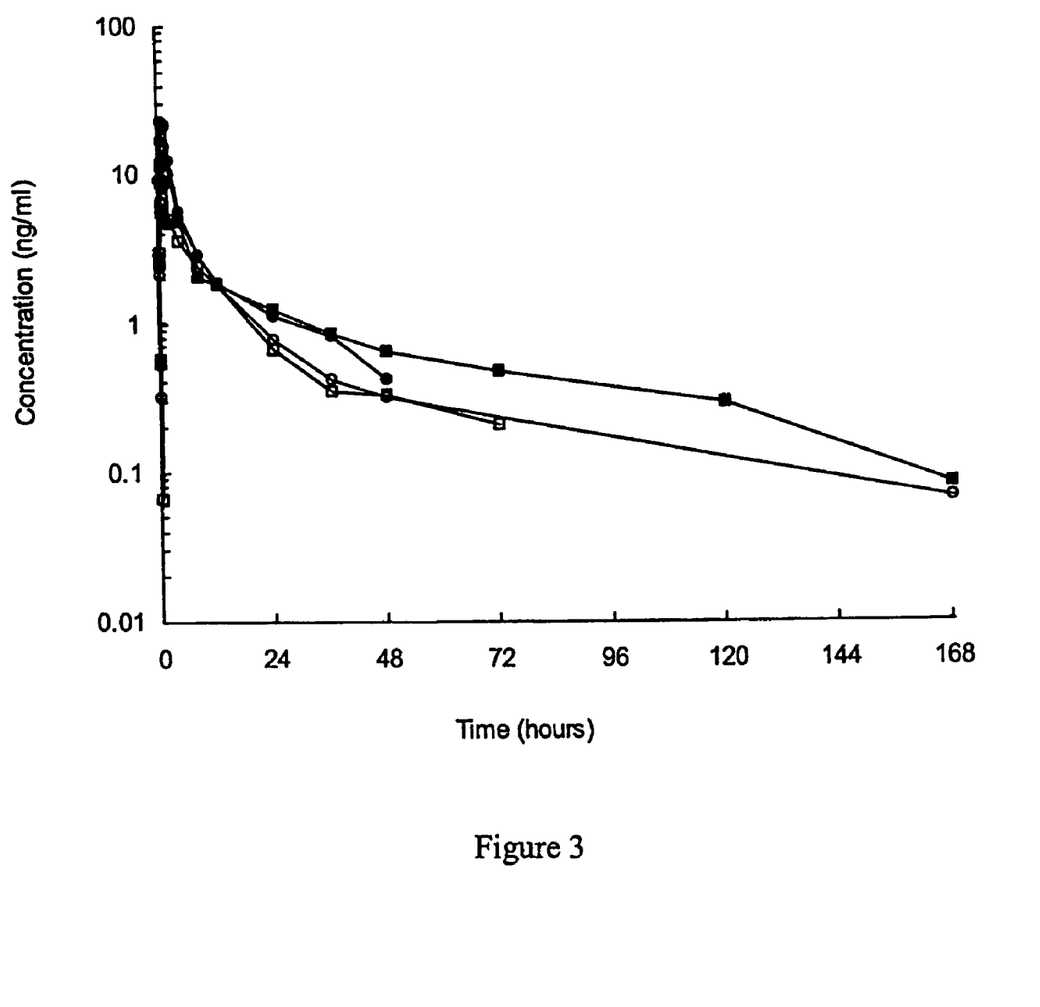
FIG. 3 depicts the plasma profiles (median values) obtained after a single subcutaneous (s.c.) administration to dogs of approximately 1 mg of [Aib$^{8,35}$]hGLP-1(7-36)NH$_2$. In each case the peptide was administered as an semisolid aqueous zinc composition as follows: solid circle: about 5% (wt/vol) peptide, peptide:Zn molar ratio about 5.4:1, no pH adjustment; open circle: about 10% (wt/vol) peptide, peptide:Zn molar ratio about 5.4:1, no pH adjustment; open square: about 10% (wt/vol) peptide, peptide:Zn molar ratio about 5.4:1, pH adjusted with NaOH; solid square: about 10% (wt/vol) peptide, peptide:Zn molar ratio about 4:1, pH adjusted with NaOH.

The compositions provided for an extended release of (Aib$^{8,35}$)hGLP1(7-36)NH$_2$, as depicted in FIG. 3.

8.6. Semisolid Compositions:

Using substantially the same in vivo assay procedure as described in section 8.1, above, the following semi-solid composition was examined for its ability to release the subject peptide over an extended period of time. This composition was formulated using a 5.22 mg/ml ZnCl$_2$ solution, at pH=2.0. Sufficient peptide was provided to result in a 25% peptide semisolid composition having a peptide to zinc ratio of about 4:1. The pH of the composition was adjusted as provided herein using 10 mg/ml NaOH. The dose of peptide administered was approximately 15 mg.

Figure 6:
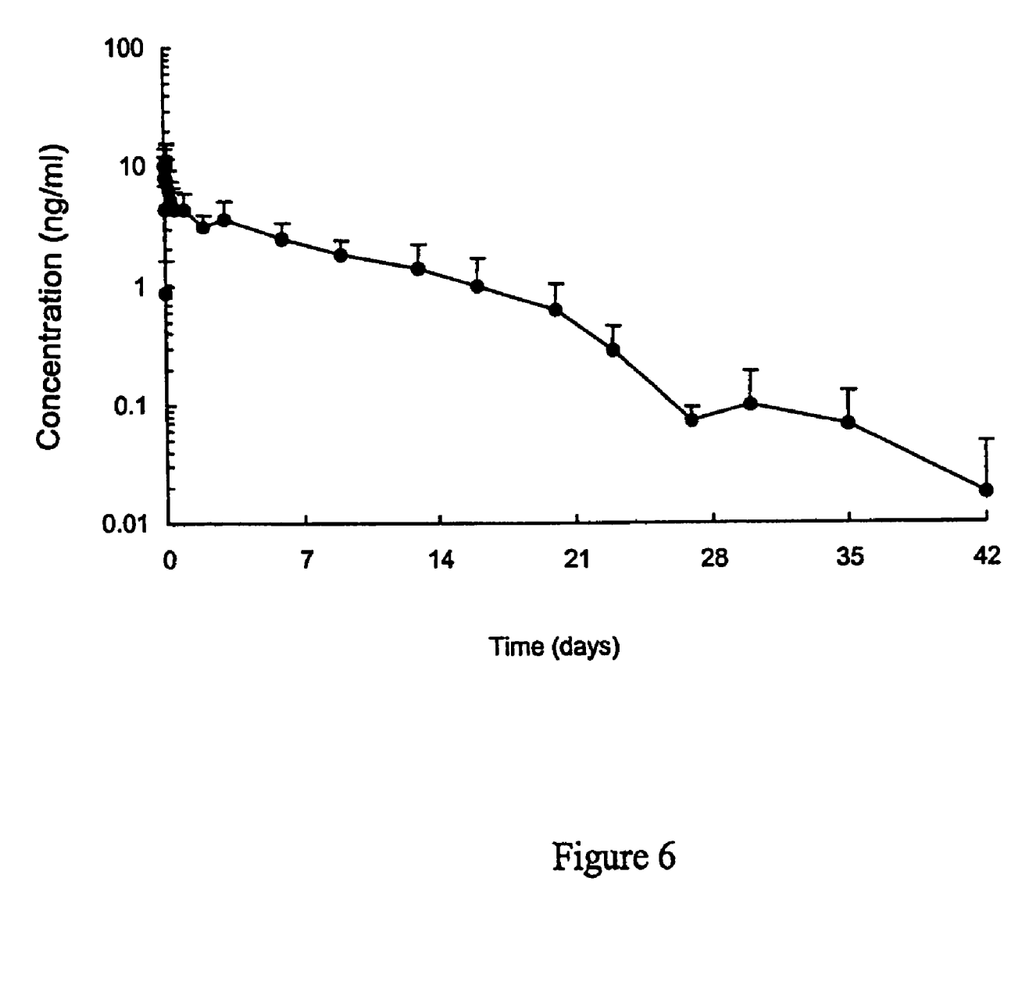
FIG. 6 depicts the plasma profiles (median values) obtained after a single subcutaneous (s.c.) administration to dogs of approximately 15 mg of [Aib$^{8,35}$]hGLP-1(7-36)NH$_2$. The peptide was administered as a semisolid zinc composition having a peptide concentration of about 25%, and a peptide:Zn molar ratio of about 4:1.

Composition 8.6 provided for an extended release of (Aib$^{8,35}$)hGLP1(7-36)NH$_2$, as depicted in FIG. 6.

8.7. Semisolid Compositions:

Using substantially the same in vivo assay procedure as described in section 8.1, above, the following semi-solid composition was examined for its ability to release the subject peptide over an extended period of time. This composition was formulated using a 8.5 mg/ml ZnCl$_2$ solution, at pH=2.0. Sufficient peptide was provided to result in a 23% peptide semisolid composition having a peptide to zinc ratio of about 1.5:1. The composition was formulated according to the process detailed in section 2.6, above. The dose of peptide administered was approximately 15 mg (corresponding to about 65 microliters of the composition).

Figure 7:
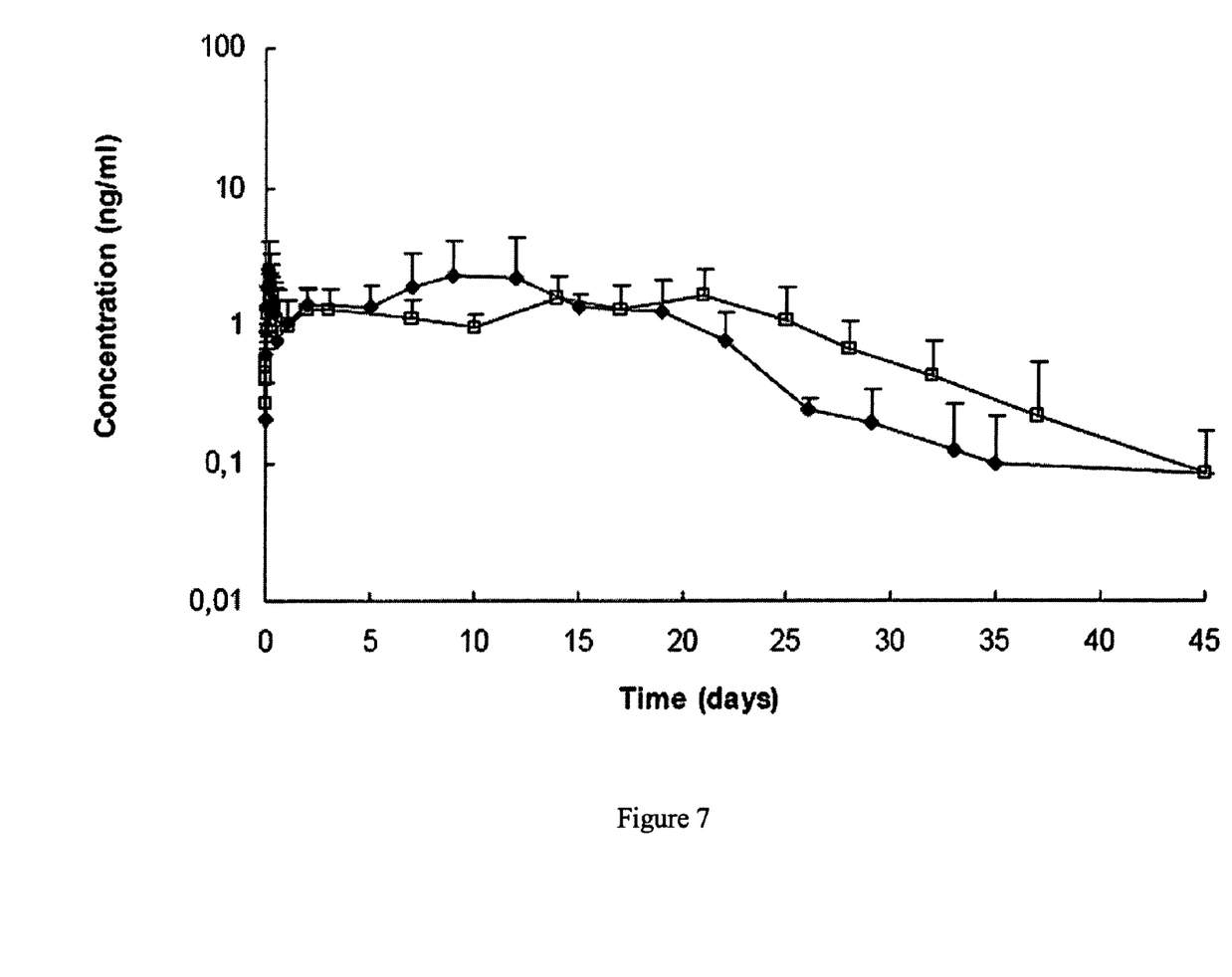
FIG. 7 depicts the plasma profiles (median values) obtained after a single subcutaneous (s.c.) administration to dogs of approximately 15 mg of [Aib$^{8,35}$]hGLP-1(7-36)NH$_2$. The peptide was administered as a semisolid zinc composition having a peptide concentration of about 23%, and a peptide:Zn molar ratio of about 1.5:1.

Composition 8.6 provided for an extended release of (Aib$^{8,35}$)hGLP1(7-36)NH$_2$, as depicted in FIG. 7.

Further assays with various permutations of the disclosed formulation have likewise been subject to in vivo assay and have confirmed that compositions of the present invention provide a useful drug delivery platform for the compound of formula (I). Using the teachings of the instant application, one skilled in the art could vary the amounts of peptide, ZnCl$_2$ and pH to prepare compositions of the present invention as described herein.

What is claimed is:

1. A pharmaceutical composition comprising an analog of glucagon-like peptide-1 according to the formula:

[Aib$^{8,35}$]hGLP-1(7-36)NH$_2$;

together with zinc and a pharmaceutically acceptable carrier or diluent, wherein said diluent comprises a pharmaceutically acceptable aqueous solution and said pharmaceutical composition is a clear solution when said composition is administered, said analog of glucagon-like peptide-1 is released within said subject for at least approximately two weeks, with the proviso that said composition does not consist of a clear aqueous ZnCl$_2$ solution having pH 4 in which said [Aib$^{8,35}$]hGLP-1(7-36)NH$_2$ is present at a concentration of 4 mg/ml and said ZnCl$_2$ is present at a concentration of 0.5 mg/ml.

2. The pharmaceutical composition according to claim 1, wherein said zinc is present in a concentration from 0.0005 mg/mL to 50 mg/mL.

3. The pharmaceutical composition according to claim 2, wherein said zinc is present in a concentration from 0.01 mg/mL to 0.50 mg/mL.

4. The pharmaceutical composition according to claim 1, wherein said diluent comprises sterile water.

5. The pharmaceutical composition according to claim 1, wherein said pharmaceutical composition comprises an aqueous mixture, suspension or solution, and wherein said analog of glucagon-like peptide-1 is present at a concentration of approximately 0.5%-30% (w/w).

6. The pharmaceutical composition according to claim 5, wherein the concentration of said analog of glucagon-like peptide-1 in said aqueous mixture, suspension or solution is approximately 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% (w/w).

7. The pharmaceutical composition according to claim 6, wherein the concentration of said analog of glucagon-like peptide-1 in said aqueous solution is approximately 1%, 2%, 3%, 4%, 5%, 6%, 7%, 8%, 9%, 10%, 11%, 14%, 15%, 16%, 19%, 20%, 21%, 22%, 23%, 24%, 25%, 26%, 29%, or 30% (w/w).

8. The pharmaceutical composition according to claim 7, wherein the concentration of said analog: of glucagon-like peptide-1 in said aqueous solution is approximately 1%, 2%, 3%, 4%, 5%, 6%, 9%, 10%, 11%, 22%, 23%, 24%, 25%, or 26% (w/w).

9. The pharmaceutical composition according to claim 8, wherein the concentration of said analog of glucagon-like peptide-1 in said aqueous solution is approximately 1%, 2%, 3%, 4%, 5%, 6%, 10%, 22%, 23%, 24%, 25%, or 26% (w/w).

10. The pharmaceutical composition according to claim 9, wherein the concentration of said analog of glucagon-like peptide-1 in said aqueous solution is approximately 1%, 2%, 5%, 10%, 23% or 25% (w/w).

11. The pharmaceutical composition according to claim 5, wherein the molar ratio of said analog of glucagon-like peptide-1 to zinc in said pharmaceutical composition ranges from approximately 6:1 to approximately 1:1.

12. The pharmaceutical composition according to claim 11, wherein said ratio ranges from approximately 5.5:1 to approximately 1:1.

13. The pharmaceutical composition according to claim 12, wherein said ratio ranges from approximately 5.4:1 to approximately 1.5:1.

14. The pharmaceutical composition according to claim 13, wherein said ratio is approximately 5.4:1, 4.0:1, or 1.5:1.

15. The pharmaceutical composition according to claim 14, wherein said ratio is approximately 1.5:1.

16. The pharmaceutical composition according to claim 5, wherein said zinc is provided as zinc chloride or zinc acetate.

17. The pharmaceutical composition according to claim 16, wherein said zinc acetate is provided as ZnAc$_2$.2H$_2$O.

18. The pharmaceutical composition according to claim 1, wherein when said composition is administered to said subject in need thereof, said analog of glucagon-like peptide-1 is released within said subject for at least approximately three weeks.

19. The pharmaceutical composition according to claim 1, wherein when said composition is administered to said subject in need thereof, the analog of glucagon-like peptide-1 is released within said subject for at least approximately four weeks.

20. The pharmaceutical composition according to claim 11, wherein when said composition is administered to said subject in need thereof, said analog of glucagon-like peptide-1 is released within said subject for at least approximately three weeks.

21. The pharmaceutical composition according to claim 11, wherein when said composition is administered to said subject in need thereof, the analog of glucagon-like peptide-1 is released within said subject for at least approximately four weeks.

22. The pharmaceutical composition according to any one of claims 18-19, wherein said subject is a mammal.

23. The pharmaceutical composition according to any one of claims 20-21, wherein said subject is a mammal.

24. The composition according to claim 15, wherein the concentration of [Aib$^{8,35}$]hGLP-1(7-36)NH$_2$ in said composition is about 1% (weight/volume).

25. The composition according to claim 15, wherein the concentration of [Aib$^{8,35}$]hGLP-1(7-36)NH$_2$ in said composition is about 2% (weight/volume).

26. The composition according to claim 15, wherein the concentration of [Aib$^{8,35}$]hGLP-1(7-36)NH$_2$ in said composition is about 10% (weight/volume).

27. The composition according to claim 15, wherein the concentration of [Aib$^{8,35}$]hGLP-1(7-36)NH$_2$ in said composition is about 25% (weight/volume).

28. The composition according to claim 14, wherein the concentration of [Aib$^{8,35}$]hGLP-1(7-36)NH$_2$ in said composition is about 5% (weight/volume) and said ratio is approximately 5.4:1.

29. The composition according to claim 14, wherein the concentration of [Aib$^{8,35}$]hGLP-1(7-36)NH$_2$ in said composition is about 5% (weight/volume) and said ratio is approximately 4.0:1.

30. The composition according to claim 14, wherein the concentration of [Aib$^{8,35}$]hGLP-1(7-36)NH$_2$ said composition is about 10% (weight/volume) and said ratio is approximately 5.4:1.

31. The composition according to claim 14, wherein the concentration of [Aib$^{8,35}$]hGLP-1(7-36)NH$_2$ in said composition is about 23% (weight/volume) and said ratio is approximately 4.0:1.

32. The composition according to claim 15, wherein the concentration of [Aib$^{8,35}$]hGLP-1(7-36)NH$_2$ in said composition is about 23% (weight/volume).

33. The pharmaceutical composition according to claim 22, wherein said subject is a human.

34. The pharmaceutical composition according to claim 23, wherein said subject is a human.

35. The composition according to claim 15, wherein the concentration of [Aib$^{8,35}$]hGLP-1(7-36)NH$_2$ in said pharmaceutical composition is about 10% (weight/volume) and the molar ratio of [Aib$^{8,35}$]hGLP-1(7-36)NH$_2$ to zinc is about 1.5:1.

36. A method of treating a subject afflicted with Type I diabetes, Type II diabetes or gestational diabetes comprising administering to said subject the pharmaceutical composition according to claim 1.

37. The method according to claim 36, wherein said subject is a human being.

38. The method according to claim 37, wherein said disease is Type I diabetes or Type II diabetes.

39. A method of stimulating beta-cell proliferation or reducing beta-cell deterioration comprising administering to a subject in need thereof the pharmaceutical composition according to claim 1.

40. The method according to claim 39, wherein said subject is a human being.

41. A method of treating a subject afflicted with Type I diabetes, Type II diabetes or gestational diabetes comprising administering to said subject the pharmaceutical composition according to claim 5.

42. The method according to claim 41, wherein said subject is a human being.

43. The method according to claim 42, wherein said disease is Type I diabetes or Type II diabetes.

44. A method of stimulating beta-cell proliferation or reducing beta-cell deterioration comprising administering to a subject in need thereof the pharmaceutical composition according to claim 5.

45. The method according to claim 32, wherein said subject is a human being.

* * * * *